US006635265B1

(12) United States Patent
Borovsky

(10) Patent No.: US 6,635,265 B1
(45) Date of Patent: Oct. 21, 2003

(54) MATERIALS AND METHODS USEFUL FOR THE CONTROL OF INSECT LARVAE

(75) Inventor: Dov Borovsky, Vero Beach, FL (US)

(73) Assignee: University of Florida Research Foundation, Inc., Gainesville, FL (US)

( * ) Notice: Subject to any disclaimer, the term of this patent is extended or adjusted under 35 U.S.C. 154(b) by 0 days.

(21) Appl. No.: 09/551,738

(22) Filed: Apr. 18, 2000

Related U.S. Application Data

(63) Continuation-in-part of application No. 09/296,113, filed on Apr. 21, 1999.

(51) Int. Cl.[7] ........................ A01N 25/00; A61K 38/04

(52) U.S. Cl. .......................... 424/405; 514/2; 530/329; 435/410; 435/418

(58) Field of Search ....................... 514/2, 15; 435/419, 435/418, 69.1, 320.1; 530/329; 536/23.1, 23.5; 424/405

(56) References Cited

U.S. PATENT DOCUMENTS 4,714,763 A 12/1987 Theodoropulos
5,011,909 A 4/1991 Borovsky et al.
5,130,253 A 7/1992 Borovsky et al.
5,250,515 A 10/1993 Fuchs et al.
5,344,821 A 9/1994 Kingan et al.
5,358,934 A * 10/1994 Borovsky et al. ............. 514/17
5,428,147 A 6/1995 Barker et al.
5,439,821 A * 8/1995 Borovsky et al. ........ 435/240.4
5,459,130 A 10/1995 Borovsky et al.
5,501,976 A * 3/1996 Borovsky et al. ........ 435/252.3
5,508,264 A 4/1996 Bradfisch et al.
5,604,121 A 2/1997 Hilder et al.
5,629,196 A * 5/1997 Borovsky et al. ........... 435/418
5,688,764 A 11/1997 Johnson et al.
5,741,669 A 4/1998 Krapcho et al.
5,753,615 A 5/1998 Thorpe et al.
5,792,750 A * 8/1998 Borovsky et al. ............. 514/16
5,800,811 A 9/1998 Hall et al.
5,849,525 A 12/1998 Hediger
6,413,530 B1 7/2002 Borovsky et al.

FOREIGN PATENT DOCUMENTS

EP 0412595 2/1991
JP 01 226898 9/1989
JP 07 188282 7/1995
WO WO 93/21217 10/1993
WO 9413698 6/1994
WO WO 95/24423 A1 9/1995
WO WO 98/21348 A1 5/1998

OTHER PUBLICATIONS

U.S. patent application Ser. No. 09/295,924, Bennett et al., filed Apr. 21, 1999.

Bylemans, D. et al. "Sequencing and characterization of trypsin modulating oostatic factor (TMOF) from the ovaries of the grey fleshfly, *Neobellieria* (Sarcophaga) *bullata*" *Regulatory Peptides*, 1994, 50:61–72.

Hua, Y–J. and J. Koolman "An ecdysiostatin from flies" *Regulatory Peptides*, 1995, 57:263–271.

Janssen, I. et al. "Biological Activity of Structural Analogs and Effect of Oil as a Carrier of Trypsin Modulating Oostatic Factor of the Gray Fleshfly *Neobellieria bullata*" *Peptides*, 1998, 19(4):627–634.

Taylor, M. and M. Lee "Trypsin Isolated from the Midgut of the Tobacco Hornworm, *Manduca Sexta*, Is Inhibited by Synthetic Pro–peptides in Vitro" *Biochemical and Biophysical Res. Comm.*, 1997, 235:606–609.

De Bolle, M. et al. "Antimicrobial peptides from *Mirabilis jalapa* and *Amaranthus caudatus*: expression, processing, localization and biological activity in transgenic tobacco" *Plant Molecular Biol.*, 1996, 31:993–1008.

Pang, S–Z et al. "Expression of a gene encoding a scorpion insectotoxin peptide in yeast, bacteria and plants" *Gene*, 1992, 116:165–172.

Bosch, D. et al. "A trout growth hormone is expressed, correctly folded and partially glycosylated in the leaves but not the seeds of transgenic plants" *Transgenic Res.*, 1994, 3:304–310.

Okamoto, M. et al. "Enhanced Expression of an Antimicrobial Peptide Sarcotoxin IA by GUS Fusion in Transgenic Tobacco Plants" *Plant Cell Physiol.*, 1998, 39(1):57–63.

Hightower, R. et al. "The expression of cecropin peptide in transgenic tobacco does not confer resistance to *Pseudomonas syringae* pv *tabaci*" *Plant Cell Reports*, 1994, 13:295–299.

Allefs, S. et al. "*Erwinia* Soft Rot Resistance of Potato Cultivars Transformed with a Gene Construct Coding for Antimicrobial Peptide Cecropin B is Not Altered" *American Potato J.*, 1995, 72:437–445.

Eipper, B. et al. "The Biosynthesis of Neuropeptides: Peptide α–Amidation" *Annu. Rev. Neurosci.*, 1992, 15:57–85.

Menn, J. and A. Borkovec "Insect Neuropeptides: Potential New Insect Control Agents" *J. Agric. Food Chem.*, 1989, 37:271–278.

Rourke, I. et al. "Heterologous Expression of Human Cholecystokinin in *Saccharomyces cerevisiae*" *The J. of Biol. Chem.*, 1997, 272(15):9720–9727.

Copley, K. et al. "Expression, processing and secretion of a proteolytically–sensitive insect diuretic hormone by *Saccharomyces cerevisiae* requires the use of a yeast strain lacking genes encoding the Yap3 and Mkc7 endoproteases found in the secretory pathway" *Biochem. J.*, 1998, 330:1333–1340.

(List continued on next page.)

*Primary Examiner*—Karen Cochrane Carlson
*Assistant Examiner*—Samuel Wei Liu
(74) *Attorney, Agent, or Firm*—Saliwanchik, Lloyd & Saliwanchik

(57) ABSTRACT

The subject invention provides materials and methods for controlling pests. In a preferred embodiment the pests are agricultural pests and, in particular, insect pests. Specifically exemplified herein are materials and methods for the control of insect larvae.

12 Claims, 1 Drawing Sheet

OTHER PUBLICATIONS

Masuda, N. et al. "Primary structure of protein moiety of *Penicillium notatum* phospholipase B deduced from the cDNA" *Eur. J. Biochem.*, 1991, 202:783–787.

Voit, R. and G. Feldmaier–Fuchs "Arthropod Hemocyanins" *The J. Biol. Chem.*, 1990, 265(32):19447–19452.

Southwick, F. and D. Purich "Inhibition of Listeria locomotion by Mosquito Oostatic Factor, a Natural Oligoproline Peptide Uncoupler of Profilin Action" *Infection and Immunity*, Jan. 1995, 63(1):182–190.

Nauen, R. et al. "TMOF–Like Factor Controls the Biosynthesis of Serine Proteases in the Larval Gut of *Heliothis virescens*" *Arch. Insect Biochem. and Physio.*, 2001, 47:169–180.

Hlavacek, J. et al. (1998) The C–terimus shortened analogs of the insect peptide oostatic hormone with accelerated activity. Biorgan. Chem. vol. 26, pp. 131–140.*

Borovksy, D., et al. [1990] "Mosquito Oostatic Factor: A Novel Decapeptide Modulating Trypsin–like Enzyme Biosynthesis in the Midgut." *FASEB Journal*, 4:3015–19.

Borovsky, D., et al. [1993] "Mass Spectrometry and Characterization of *Aedes aegypti* Trypsin Modulating Oostatic Factor (TMOF) and its Analogs." *Insect Biochem. Molec. Biol.*, 23(6):703–712.

Bordusa, F., et al. [1998] "The Specificity of Prolyl Endopeptidase from *Flavobacterium meningoseptum*: Mapping the S' Subsites by Positional Scanning via Acyl Transfer." *Bioorganic & Medicinal Chemistry*, 6:1775–1780.

Deslauriers, R., et al. [1979] "Steric Effects of cis–trans Isomerism on Neighboring Residues in Proline Oligopeptides: A 13C–NMR Study of Conformational Heterogeneity in Linear Tripeptides." *Biopolymers*, 18:523–538.

Ganthier, A. J. [1995] "Direct Submission." *Plant Physiol.*, 3:108,1341.

Henderson, D., et al. [1990] "Physicochemical Studies of Biologicaly Active Peptides by Low–Temperature Reversed–phase High–performance liquid Chromatography." *Chemical Abstracts*, 112:86.

Hlavacek, J., et al. [1998] "the C–Terminus Shortened Analogs of the Insect Peptide Oostatic Hormone with Accelerated Activity." *Bioorganic Biochemistry*, 26:131–140 (article BH981092).

Narberhaus, F., et al. [1996] "The *Bradyrhizobium japonicum* rpoH1 Gene Encoding a Sigma 32–like Protein is Part of a Unique Heat Shock Gene Cluster Tgether with groESL1 and Three Small Heat Shock Genes." *J. Bacteriol.* 18:178, 5337–5346.

Shibnev, V.A., et al. [1969] "Synthesis of Monmers that are Triplets of the 'Crystalline' Part of the Collagen Molecule." *Chemical Abstracts*, 70(25).

Tykva et al. (Jun. 26, 2000) "The fate of an oostatic peptide or its analogs including metabolites in insects Diptera and Orthoptera and its transformation to the next generation" *Chemical Abstracts* vol. 132(26), abstract No. 345576.

U.S. patent application Ser. No. 10/062,623, Borovsky et al., filed Jan. 31, 2002.

U.S. patent application Ser. No. 09/551,737, Borovsky et al., filed Apr. 18, 2000.

U.S. patent application Ser. No. 09/295,846, Borovsky, filed Apr. 21, 1999.

Borovsky, D. et al. "Mosquito Oostatic Hormone" *Insect Neuropeptides: Chemistry, Biology Action*, 1991, 135–142.

Borovsky, D. et al. "Development of Specific RIA and ELISA to Study Trypsin Modulating Oostatic Factor in Mosquitoes" *Archives of Insect Biochemistry and Physiology*, 1992, 21:13–21.

Charbonneau, H. "Strategies for Obtaining Partial Amino Acid Sequence Data from Small Quantities (>5nmol) of Pure or Partially Purified Protein" A Practical Guide to Protein and Peptide Purification for Microsequencing, 1989, pp. 15–30.

Hlavacek et al. "Synthesis, radiolabeling and biological activity of peptide oostatic hormone and its analogues" *J. Peptide Res.*, 1997, 50:153–158.

Kolaskar, A.S. and V. Ramabrahmam "Conformational properties of pairs of amino acids" *Int. J. Peptide Protein Res.*, 1983, 22:83–91.

Ladram et al. "Characterization of receptors for thyrotropin–releasing hormone–receptors potentiating peptide on rat anterior pituitary membranes" *J. Biol. Chem.*, 1992, 267(36):25697–25702.

Merkler et al. "C–Terminal amidated peptides: Production by the in vitro enzymatic amidation of glycine–extended peptides and the importance of the amide to bioactivity" *Enzyme*, 1994, 16(6):450–456.

Okada et al. "Synthesis of bradykinin fragments and their effect on pentobarbital sleeping time in mouse" *Chemical Abstracts*, Nov. 7, 1977, 87(19), abstract No. 146142, abstract only.

Pauletti et al. "Structural requirements for intestinal absorption of peptide drugs" *J. Controled Rel.*, 1996, 41:3–17.

Rao, R. et al. "Synthesis and expression of genes encoding putative insect neuropeptide precursors in tobacco" *Gene*, 1996, 175:1–5.

Rayne, R.C. and M. O'Shea "Inactivation of Neuropeptide Hormones (AKH I and AKH II) Studied In Vivo and In Vitro" *Insect Biochem. Molec.*, 1992, 22(1):25–34.

Rudinger "Characteristics of the amino acids as components of a peptide hormone sequence" Jun. 1976, pp. 1–7, In Peptide Hormones, Parsons (ed.), University Park press, Baltimore.

Schwartz, J.C. et al. "Biological Inactivation of Enkephalins and the Role of Enkephalin–Dipeptidyl–Carboxypeptidase ("Enkephalinase") as Neuropeptidase" *Life Sciences*, 1981, 29:1715–1740.

Sober, H.A. "Handbook of Biochemistry" the Chemical Rubber Co., Cleveland, Ohio, 1968, p. C70.

Tortiglione, C. et al., "New genes for pest control" *Genetics and Breeding for Crop Quality and Resistance*, Jul. 1999, (Abstract).

Tortiglione, C. et al., "New genes for pest control" *Genetics and Breeding for Crop Quality and Resistance*, Jul. 1999, (Full–text).

Borovsky, Dov (1985) "Isolation and Characterization of Highly Purified Mosquito Oostatic Hormone" *Archives of Insect Biochemistry and Physiology* 2:333–349.

Borovsky, Dov (1988) "Oostatic Hormone Inhibits Biosynthesis of Midgut Proteolytic Enzymes and Egg Development in Mosquitoes" *Archives of Insect Biochemistry and Physiology* 7:187–210.

Borovsky, Dov, C.A. Powell, J.K. Nayar, J. Edwin Blalock, T.K. Hayes (1994) "Characterization and localization of mosquito–gut receptors for trypsin modulating oostatic factor using a complementary peptide and immunocytochemistry" *The FASEB Journal* 8:350–355.

Borovsky, Dov, Farida Mahmood (1995) "Feeding the mosquito *Aedes aegypti* with TMOF and its analogs; effect on trypsin biosynthesis and egg development" *Regulatory Peptides* 57:273–281.
Curry, W.J., C. Shaw, C.F. Johnston, L. Thim, K.D. Buchanan (1992) "Neuropeptide F: Primary Structure From The Tubellarian, *Artioposthia Triangulata" Comp. Biochem. Physiol.* 101C(2):269–274.
Duve, Hanne, Alan Thorpe, Ray Neville, Norman R. Lazarus (1981) "Isolation and partial characterization of pancreatic polypeptide–like material in the brain of the blowfly *Calliphora vomitoria" J. Biochem.* 197:767–770.
Leung, P.S., C. Shaw, A.G. Maule, L. Thim, C.F. Johnston, G.B. Irvine (1992) "The primary structure of neuropeptide F (NPF) from the garden snail, *Helix aspersa" Regulatory Peptides* 41:71–81.
Maule et al. (1991) "Neuropeptide F: a novel parasitic flatworm regulatory peptide from *Moniezia expansa* (Cestoda: Cyclophyllidea)" *Parasitology* 102:309–316.
Rajpara, Sanjay M., et al. (1992) "Identification and Molecular Cloning of a Neuropeptide Y Homolog That Produces Prolonged Inhibition in Aplysia Neurons" *Neuron* 9:505–513.
Spittaels, Kurt, Peter Verhaert, Christ Shaw, Richard N. Johnston, Bart Devreese, Jos Van Beeumen, Arnold De Loof (1996) "Insect Neuropeptide F (NPF)–related Peptides: Isolation from Colorado Potato Beetle (*Leptinotarsa decemlineata*) Brain" *Insect Biochem. Molec. Biol.* 26(4):375–382.

Veenstra, J.A., H.M. Romberg–Privee, H. Schooneveld, J.M. Polak (1985) "Immunocytochemical localization of peptidergic neurons and neurosecretory cells in the neuro–endocrine system of the Colorado potato beetle with antisera to vertebrate regulatory peptides" *Histochemistry* 82:9–18.

Verhaert, Peter, Cornelis J. P. Grimmelikhuijzen, Arnold De Loof (1985) "Distinct Localization of FMRFamide– and Bovine Pancreatic Polypeptide–Like Material in the Brain, Retrocerebral Complex and Suboesophageal Ganglion of the Cockroach *Periplaneta americana* L." *Brain Research* 348:331–338.

* cited by examiner

MATERIALS AND METHODS USEFUL FOR THE CONTROL OF INSECT LARVAE

CROSS-REFERENCE TO A RELATED APPLICATION

This application is a continuation-in-part of U.S. patent application Ser. No. 09/296,113, filed on Apr. 21, 1999.

The subject invention was made with government support under research projects supported by NIH Grant No. AI041254 and USDA/FAES/FME-03249. The government has certain rights in this invention.

BACKGROUND OF THE INVENTION

Many blood-sucking pests are known to attack humans and animals. Many of these are vectors for pathogenic microorganisms which threaten human health and commercially important livestock and pets. Various species of mosquitoes transmit diseases caused by viruses and many are vectors for disease-causing nematodes and protozoa. For example, mosquitoes of the genus Anopheles transmit malaria which causes approximately 1 million deaths annually. The mosquito species *Aedes aegypti* transmits an arbovirus that causes the disease yellow fever in humans. Other arboviruses transmitted by Aedes species include those that cause dengue fever, eastern and western encephalitis, Venezuelan equine encephalitis, St. Louis encephalitis, chikungunya, oroponehe and bunyarnidera. The genus Culex, which includes the common house mosquito *C. pipiens*, is implicated in the transmission of various forms of encephalitis and filarial worms. The common house mosquito also acts as a vector for *Wuchereria banuffi* and *Brugia malayi*, which are responsible for lymphatic filariasis. *Trypanasomas cruzi*, the causative agent of Chagas' disease is transmitted by various species of blood-sucking Triatominae bugs. The tsetse fly (Glossina Spp.) acts as a vector for African trypanosomal diseases of humans and cattle. Many other diseases are transmitted by various blood-sucking pest species. Many of the blood-sucking pests are found within the order Diptera, including, for example, mosquitoes, black flies, no-see-ums (punkies), horse flies, deer flies and tsetse flies.

Various pesticides have been employed in efforts to control or eradicate populations of disease-bearing pests, such as disease-bearing blood-sucking pests. For example, DDT, a chlorinated hydrocarbon, has been used in attempts to eradicate malaria-bearing mosquitoes throughout the world. Other examples of chlorinated hydrocarbons, are BHC, lindane, chlorobenzilate, methoxychlor, and the cyclodienes (e.g., aldrin, dieldrin, chlordane, heptachlor, and endrin). The long-term stability and tendency of many of these pesticides to bioaccumulate render them particularly dangerous to the environment.

Another common class of pesticides is the organophosphates, which is perhaps the largest and most versatile class of pesticides. Organophosphates include, for example, parathion, Malathion, diazinon, naled, methyl parathion, and dichlorvos. Organophosphates are generally much more toxic than the chlorinated hydrocarbons. Their pesticidal effect is based on their ability to inhibit the enzyme cholinesterase, an essential enzyme in the functioning of the insect nervous system. However, they are also toxic to many animals, including humans.

The carbamates, a relatively new group of pesticides, include such compounds as carbamyl, methomyl, and carbofuran. These compounds are rapidly detoxified and eliminated from animal tissues. Their toxicity is thought to involve a mechanism similar to the mechanism of the organophosphates consequently they exhibit similar shortcomings, including animal toxicity.

A major problem in pest control results from the capability of many species to develop resistance. This resistance results from the selection of naturally occurring mutants possessing biochemical, physiological or behavioristic factors that confer some degree of immunity. Species of Anopheles mosquitoes have been known to develop resistance to DDT and dieldrin, the original pesticides used for house spraying. Substitute pesticides that are effective include Malathion, propoxur and fenitrothion; yet the cost of these pesticides is much greater than the cost of DDT.

Many pests, such as blood-sucking pests, require a proteinaceous meal to provide free amino acids that are necessary for egg development. The existence of oostatic hormones that inhibit digestion of the protein meal and thereby inhibit egg development has been demonstrated in various species, including house flies and mosquitoes.

In 1985, Borovsky purified an oostatic hormone 7,000-fold and disclosed that injection of a hormone preparation into the body cavity of blood imbibed mosquitoes caused inhibition of egg development and sterility (Borovsky, D. [1985] *Arch. Insect Biochem. Physiol.* 2:333–349). Following these observations, Borovsky (Borovsky, D. [1988] *Arch. Ins. Biochem. Physiol.* 7:187–210) disclosed that injection or passage of a peptide hormone preparation into mosquitoes inhibited the biosynthesis of serine esterase, trypsin-like and chymotrypsin-like enzymes in the epithelial cells of the gut, causing inefficient digestion of the blood meal and a reduction in the availability of free amino acids translocated by the hemolymph. Such amino acids are needed for the yolk protein synthesis in the fat body. When yolk protein is not synthesized yolk is not deposited in the ovaries, resulting in arrested egg development in the treated insect. It has been observed that the oostatic hormone peptides do not have an effect when inside the gut or other parts of the digestive system (Borovsky, D. [1988], supra).

In the mosquito *Aedes aegypti*, an early trypsin that is found in the midgut of newly emerged females is replaced, following the blood meal, by the late trypsin that is synthesized in a very short time; a female mosquito weighs 2 mg and produces 4 to 6 $\mu$g trypsin within several hours after the blood meal. If trypsin would continue to be synthesized at this rate, female mosquitoes would spend all their energy on trypsin biosynthesis and would neither be able to mature their eggs nor find an oviposition site. To conserve energy the mosquito regulates trypsin biosynthesis with a hormone named Trypsin Modulating Oostatic Factor (TMOF). TMOF is synthesized in the follicular epithelium of the ovary 2–30 hours after a blood meal and is released in to the hemolymph, binding to a specific receptor on the midgut epithelial cells signaling the termination of trypsin biosynthesis. Mosquito larvae also synthesize trypsin as their major protease and use the enzyme to digest decaying organic material or small organisms like algae that are found in ponds and marshes.

Following the initial report by Borovsky in 1985, the isolated 10 amino acid hormone, trypsin modulating oostatic factor (TMOF) was isolated. TMOF (YDPAP$_6$) (SEQ ID NO. 8) and two analogs (DYPAP$_6$ and PAP$_6$) (SEQ ID NOs. 9 and 10) of that peptide, were disclosed in U.S. Pat. Nos. 5,011,909 and 5,130,253, and in a 1990 publication (Borovsky, D., D. A. Carlson, P. R. Griffin, J. Shabanowitz, D. F. Hunt [1990] *FASEB J.* 4:3015–3020).

U.S. Pat. No. 5,358,934 discloses truncated forms of the full length TMOF which have prolines removed from the C terminus, including the peptides YDPAP (SEQ ID NO. 11), YDPAPP (SEQ ID NO. 12), YDPAPPP (SEQ ID NO. 13), and YDPAPPPP (SEQ ID NO. 14).

Neuropeptides Y (NPY) are an abundant family of peptides that are widely distributed in the central nervous system of vertebrates. In invertebrates members of NPY family have been recently isolated and their structures have been determined in a cestode and a turbellarian, respectively (Maule et al., 1991 "Neuropeptide F: A Novel Parasitic Flatworm Regulatory Peptide from *Moniezia expansa* (Cestoda: Cyclophylidea)" Parasitology 102:309–316; Curry et al., 1992 "Neuropeptide F: Primary Structure from the Turbellarian, *Arthioposthia triangulata*" Comp. Biochem. Physiol. 101C:269–274) and in terrestrial and marine molluscs (Leung et al., 1992 "The Primary Structure of Neuropeptide F (NPF) from the Garden Snail, *Helix aspersa*" Regul. Pep. 41:71–81; Rajpara et al., 1992 "Identification and Molecular Cloning of Neuropeptide Y Homolog that Produces Prolonged Inhibition in aplysia Neurons" Neuron. 9:505–513). The invertebrate NPYs exhibit high homology to vertebrate NPYs at the carboxyl terminus. The major difference between vertebrate and invertebrate NPYs at the C-terminus is that the vertebrate NPY has an amidated tyrosine (Y) whereas invertebrates have an amidated phenyl alanine (F). Because of this difference, the invertebrate peptides have been named NPF.

Cytoimmunochemical analyses of the NPY family members suggest that they are concentrated in the brain of various insects (Verhaert et al., 1985 "Distinct Localization of FMRFamide- and Bovine Pancreatic Polypeptide-Like Material in the Brain, Retrocerebal Complex and Subesophageal Ganglion of the Cockroach *Periplaneta americana*" L. Brain Res. 348:331–338) including the Colorado potato beetle *Leptinotarsa decemlineata* (Veenstra et al., 1985 "Immunocytochemical Localization of Peptidergic Neurons and Neurosecretory Cells in the Neuro-Endocrine System of the Colorado Potato Beetle with Antisera to Vertebrate Regulatory Peptides" Histochemistry 82:9–18). Partial purification of the members of the NPY family in insects suggests that both NPY and NPF are synthesized in insects (Duve et al., 1981 "Isolation and Partial Characterization of Pancreatic Polypeptide-like Material in the Brain of the Blowfly *alliphora vomitoria*" Biochem. J. 197, 767–770).

Recently two novel neuropeptides with NPF-like immunoreactivity have been isolated from brain extracts of the Colorado potato beetle. The peptides were purified using $C_{18}$ reversed phase HPLC and their structure was determined using mass spectrometry. The deduced structures of these peptides are: Ala-Arg-Gly-Pro-Gln-Leu-Arg-Leu-Arg-Phe-(ARGPQLRLRFamide) (SEQ ID NO. 1) and Ala-Pro-Ser-Leu-Arg-Leu-Arg-Phe-(APSLRLRFamide) (SEQ ID NO. 2) and were designated as NPF I and NPFII, respectively (Spittaels, Kurt, Peter Verhaert, Chris Shaw, Richard N. Johnston et al. [1996] *Insect Biochem. Molec. Biol.* 26(4):375–382).

The widespread use of pesticides has resulted in growing environmental and health care concerns about the use of pesticides. Many pesticides are detrimental to humans, either directly during application, or indirectly through residues in food, water and the environment. There is clearly a longstanding need in the art for pesticidal compounds which are specific and which reduce or eliminate direct and/or indirect threats to human health posed by currently available pesticides. There is, therefore, a need for environmentally compatible, biodegradable, pest-specific pesticides that can effectively deplete or eliminate pests.

BRIEF SUMMARY OF THE INVENTION

The subject invention provides materials and methods for controlling pests. In a preferred embodiment the pests are agriculture pests, and, in particular, insects. Specifically exemplified herein are materials and methods for the control of insect larvae.

In a preferred embodiment, the subject invention concerns a plant cell transformed to express a polynucleotide encoding a pesticidal agent capable of inhibiting trypsin biosynthesis. Ingestion of the transgenic plant cell by a pest causes a decrease in trypsin synthesis in the gut of the pest. This decrease in trypsin synthesis drastically slows down the breakdown of food resulting in starvation, and eventually death of the pest. Pesticidal agents useful according to the subject invention include, but are not limited to, TMOF and functional equivalents thereof, NPF and functional equivalents thereof, and other agents identifiable by, for example, assays employing a TMOF receptor.

One embodiment of the present invention concerns a pesticide composition comprising a peptide having the formula:

$$A^1A^2A^3A^4A^5Fl \quad \text{(Formula I) (SEQ ID NO. 5)}$$

wherein:

- $A^1$ is selected from the group consisting of Y, A, D, F, G, M, P, S and Y;
- $A^2$ is selected from the group consisting of A, D, E, F, G, N, P, S and Y;
- $A^3$ is selected from the group consisting of A, D, F, G, L, P, S and Y;
- $A^4$ is optionally present when $A^3$ is present and is selected from the group consisting of A, F, G, L and Y;
- $A^5$ is optionally present when $A^4$ is present and is selected from the group consisting of A, F, L and P;
- Fl is a flanking region which is optionally present and is selected from the group consisting of: P, PP, PPP, PPPP (SEQ ID NO. 6), and PPPPP (SEQ ID NO. 7).

In a more specific aspect the peptide or protein comprises an amino acid sequence which consists essentially of the amino acid sequence of Formula I. In a preferred aspect, the peptide or protein lacks TMOF amino acids adjacent to the amino acid sequence of Formula I. In still another aspect, the peptide consists of the amino acid sequence of Formula I.

In various embodiments, either $A^3A^4A^5$, $A^3A^4A^5Fl$, $A^4A^5$, $A^4A^5Fl$, $A^5$ or $A^5Fl$ are no present. Where $A^5$ is not present, Fl may be attached directly to $A^4$. Where $A^4A^5$ is not present, Fl may be attached directly to $A^3$. Finally, where $A^3A^4A^5$ is not present, Fl may be attached directly to $A^2$.

Preferred peptides are selected from the group consisting of: AAP (SEQ ID NO. 16), ADP (SEQ ID NO. 17), ADPAP (SEQ ID NO. 18), APA (SEQ ID NO. 19), DAA (SEQ ID NO. 20), DF (SEQ ID NO. 21), DPA (SEQ ID NO. 22), DY (SEQ ID NO. 23), DYP (SEQ ID NO. 24), FAP (SEQ ID NO. 25), FDP (SEQ ID NO. 26), FDPAP (SEQ ID NO. 27), FSP (SEQ ID NO. 28), MPDYP5 (SEQ ID NO. 29), PAA (SEQ ID NO. 30), PAP (SEQ ID NO. 31), Y(D)DP (SEQ ID NO. 32), Y(D)DPAP (SEQ ID NO. 33), YAP (SEQ ID NO. 34), YD (SEQ ID NO. 35), YDA (SEQ ID NO. 36), YDAAP (SEQ ID NO. 37), YDF (SEQ ID NO. 38), YDFAP (SEQ ID NO. 39), YDG (SEQ ID NO. 40), YDLAP (SEQ ID NO. 41), YDP (SEQ ID NO. 42), (D)YDP (SEQ ID NO. 43), YDPAF (SEQ ID NO. 44), YDPAL (SEQ ID NO. 45), (D)YDPAP (SEQ ID NO. 46), YDPFP (SEQ ID NO. 47), YDPGP (SEQ ID NO. 48), YDPLP (SEQ ID NO. 49), YEPAP (SEQ ID NO. 50), YFPAP (SEQ ID NO. 51), YNPAP (SEQ ID NO. 52) and YSF (SEQ ID NO. 53).

A further embodiment of the present invention comprises a peptide having the formula $A^1A^2$ (Formula II) (SEQ ID NO. 63)

wherein $A^1$ is an amino acid selected from the group consisting of A, D, F, M, and Y, and $A^2$ is an amino acid selected from the group consisting of A, D, E, P, and Y.

In a preferred embodiment, the subject invention is directed to peptides of Formula II wherein $A^1$ and $A^2$ are independently selected from the group consisting of A, D, and Y.

Specifically exemplified as another embodiment are methods using an NPF peptide having the sequence Ala-Arg-Gly-Pro-Gln-Leu-Arg-Leu-Arg-Phe-$NH_2$ (SEQ ID NO. 1) or Ala-Pro-Ser-Leu-Arg-Leu-Arg-Phe-$NH_2$ (SEQ ID NO. 2).

The biological control agents also comprise fragments, derivatives and analogs of NPF and TMOF peptides including, for example, NPF and/or TMOF peptides in which only conservative substitutions have been made. Analogs of the above-mentioned proteins and peptides which have one or more amino acid substitutions forming a branched peptide (e.g., by substitution with an amino acid or amino acid analog having a free amino- or carboxy-side chain that forms a peptide bond with a sequence of one or more amino acids, including but not limited to prolines) or allowing circularization of the peptide (e.g., substitution with a cysteine, or insertion of a cysteine at the amino- or carboxy-terminus or internally), to provide a sulfhydryl group for disulfide bond formation, are also provided.

The peptides of the present invention are particularly advantageous because their smaller size permits more rapid and efficient penetration into the midgut. In addition, they are less expensive to produce by conventional chemical methods.

In one embodiment, the subject invention provides pesticidal polypeptides having a C-terminus arginine. In a preferred embodiment, these short polypeptides can be joined to form polymers of repeating units. Specifically exemplified herein is the $(DPAR)_4$ (SEQ ID NO. 61) polymer which can be broken into four DPAR (SEQ ID NO. 60) units in the gut of the pest. Advantageously, the short pesticidal polypeptides connected by arginine (or other readily cleavable residue) can penetrate the midgut of the pest efficiently.

Also included in this invention are addition salts, complexes, or prodrugs such as esters of the NPF and TMOF peptides, especially the nontoxic pharmaceutically or agriculturally acceptable acid addition salts. The acid addition salts can be prepared in standard manner in a suitable solvent from the parent compound and an excess of an acid, such as hydrochloric, hydrobromic, sulfuric, phosphoric, acetic, maleic, succinic, ethanedisulfonic or methanesulfonic acids. Also, the N-terminus and C-termninus of the peptides can be chemically modified to further inhibit proteolysis by metabolic enzymes.

The NPF and TMOF peptides can also be synthesized wherein at least one of the amino acids is in the D-configuration, as opposed to the naturally occurring L-amino acids. The presence of D-configuration amino acids can inhibit the ability of proteases to degrade the peptides of the subject invention.

Also, derivation of these compounds with long chain hydrocarbons will facilitate passage through the cuticle into the pest body cavity. Therefore, a further embodiment of the subject invention pertains to compositions comprising the NPF and/or TMOF peptides bound to lipids or other carriers.

Yet another aspect of the subject invention pertains to polynucleotide sequences encoding the peptides disclosed herein. These DNA sequences can easily be synthesized by a person skilled in the art. The sequences may be used to transform an appropriate host to confer upon that host the ability to express the pesticidal peptides. Hosts of particular interest include bacteria, algae, yeasts, insect viruses, and plants. For each of these hosts, the polynucleotide sequences may be specifically designed by a person skilled in the art to utilize codons known to be optimally expressed in the particular hosts. Advantageous promoters can also easily be utilized. Bacteria, yeasts, plants, algae, viruses, and other hosts each may be used to produce peptides for further use, or these hosts can be used as vehicles for direct application of the peptide to the target pest. Plants can be transformed so as to make the plant toxic to a target pest species which feeds on that plant. Methods for transforming plant cells utilizing, for example agrobacteria, are well known to those skilled in the art.

The subject invention provides pest control compositions wherein the pest control agents are formulated for application to the target pests, or their situs. In a specific embodiment, recombinant hosts, which express a pest control agent are provided by the subject invention. The recombinant host may be, for example, procaryotic or eucaryotic.

Preferably, the subject peptides have an $LD_{50}$ against pest larvae of less than 3.0 moles/ml. More preferably, the peptides have an $LD_{50}$ of less than 2.0 moles/ml, and, most preferably, the peptides have an $LD_{50}$ of less than 1.0 moles/ml. As used herein, "$LD_{50}$"" refers to a lethal dose of a peptide able to cause 50% mortality of larvae maintained on a diet of 1 mg/ml autoclaved yeast (Borovsky and Mahmood [1995] "Feeding the mosquito *Aedes aegypti* with TMOF and its analogs; effect on trypsin biosynthesis and egg development," *Regulatory Peptides* 57:273–281).

Another aspect of the subject invention relates to a plant comprising a plant cell transformed to express a polynucleotide encoding for a pesticidal agent of the subject invention. Further, the invention provides a plant tissue comprising a plant cell transformed to express a polynucleotide encoding a pesticidal agent of the subject invention.

A further aspect of the subject invention pertains to a method of increasing the pest-resistance of a plant comprising transforming a plant cell to express a polynucleotide encoding a pesticidal agent of the subject invention and culturing said plant cell. Preferably, the method further comprises regenerating a plant from the plant cell, wherein the plant comprises a plant cell expressing a polynucleotide encoding a pesticidal agent.

Yet an additional aspect of the subject invention pertains to a method of controlling agricultural pests comprising administering to the pests a pesticidal agent of the subject invention.

Still a further aspect of the subject invention concerns a method of controlling agricultural pests comprising transforming a microbe to express a polynucleotide encoding a pesticidal agent of the subject invention and administering the microbe to the pests.

The methods and materials of the subject invention provide a novel means for controlling agricultural pests and alleviating the destruction they can cause. In a preferred embodiment, the pesticidal agents of the subject invention disrupt the food digestion and egg production of the pests. Since the targets of the pesticidal agents can include receptors intrinsic to the survival of the pest, it will be very difficult for the pests to adapt and become resistant to the pesticidal materials and methods of the subject invention. This is a marked improvement over currently available agents and methods to which pests have already begun to develop resistance.

As used herein, the term "pesticidally effective" is used to indicate an amount or concentration of a pesticide which is sufficient to reduce the number of pests in a geographical area, as compared to a corresponding geographical area in the absence of the amount or concentration of the pesticide.

The term "pesticidal" is not intended to refer only to the ability to kill pests, but also includes the ability to interfere with a pest's life cycle in any way that results in an overall reduction in the pest population. For example, the term "pesticidal" includes inhibition or elimination of reproductive ability of a pest, as well as inhibition of a pest from progressing from one form to a more mature form, e.g., transition between various larval instars or transition from larva to pupa or pupa to adult. Further, the term "pesticidal" is intended to encompass all phases of a pest life cycle; thus, for example, the term includes larvicidal and ovicidal actions.

The word "transform" is broadly used herein to refer to introduction of an exogynous polynucleotide sequence into a prokaryotic or eukaryotic cell by any means known in the art (including for example, direct transmission of a polynucleotide sequence from a cell or virus particle as well as transmission by infective virus particles) resulting in a permanent or temporary alteration of genotype and in an immortal or non-immortal cell.

The terms "peptide," "polypeptide," and "protein" as used herein are intended to refer to amino acid sequences of any length.

BRIEF DESCRIPTION OF THE SEQUENCES

Figure 1:
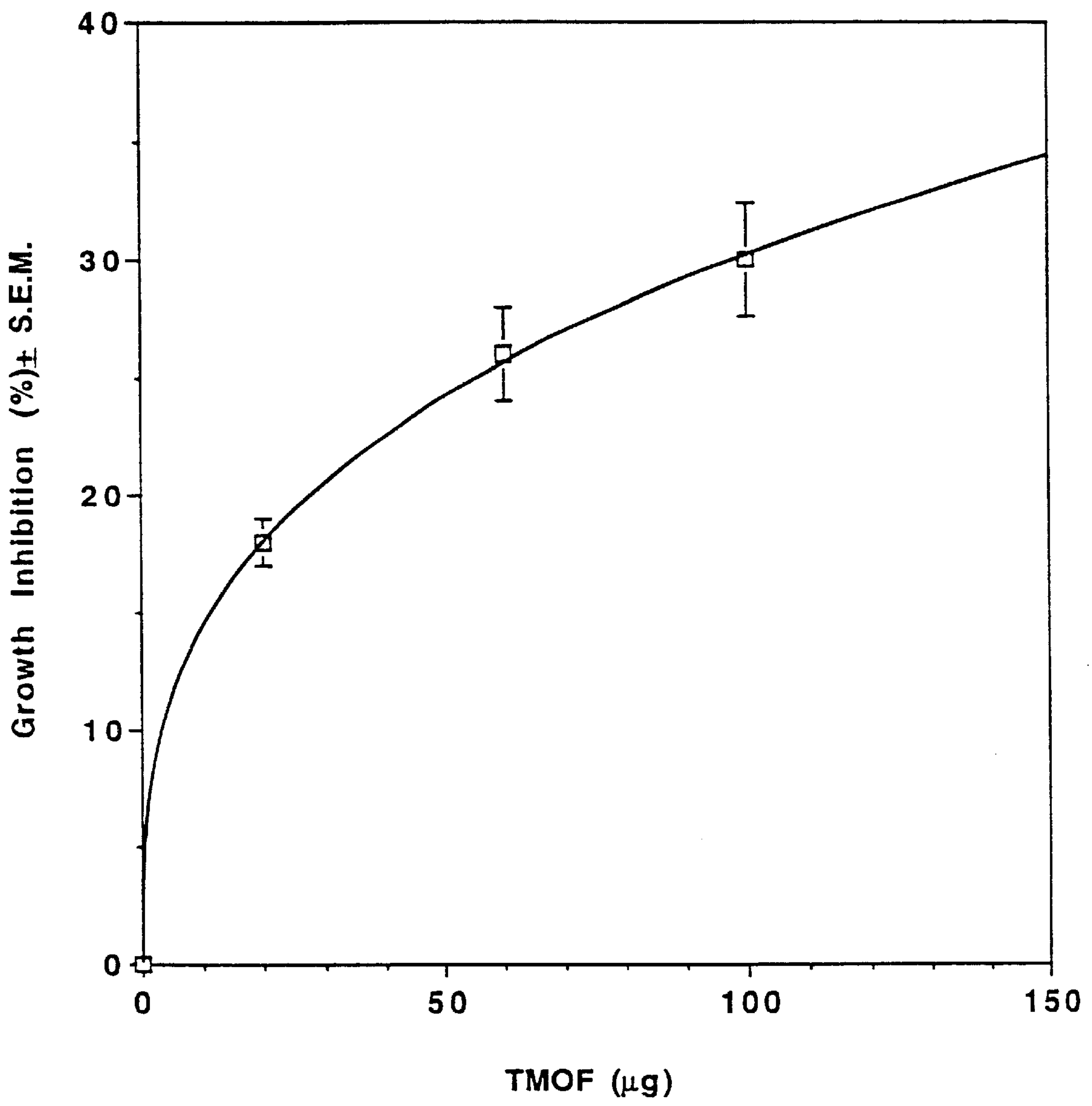
FIG. 1 shows the inhibition of growth of *S. exigua* caused by oral administration of TMOF. The x-axis represents the TMOF concentration and the y-axis represents percentage of growth inhibition.

SEQ ID NO. 1 is a neuropeptide designated NPF I.

SEQ ID NO. 2 is a neuropeptide designated NPF II.

SEQ ID NO. 3 is a polynucleotide encoding an amino acid sequence of a TMOF receptor.

SEQ ID NO. 4 is an amino acid sequence of a TMOF receptor.

SEQ ID NO. 5–56 are TMOF peptides useful according to the subject invention.

SEQ ID NOS. 57–61 are trypsin modulating oostatic factor-R analogue peptides useful according to the subject invention.

SEQ ID NOS. 62–63 are TMOF peptides useful according to the subject invention.

DETAILED DISCLOSURE OF THE INVENTION

The subject invention is directed to novel materials and methods for the control of pests. Specifically exemplified herein are recombinant hosts, including plants and microbes, transformed to express a pesticidal agent. Preferably, the pesticidal agent is capable of inhibiting trypsin biosynthesis in insects.

The term "pest(s)" as used herein includes insects and other organisms which adversely affect, humans, plants or animals. Pests controlled according to the subject invention include those which have a mechanism for regulating trypsin concentrations in the gut which involves the binding of a ligand to a receptor to increase digestive enzymes, e.g., TMOF binding to its receptor. Examples of pests which can be controlled according to the subject invention include, but are not limited to, lepidopterans, coleopterans, and other pests which attack plants.

In one embodiment, the subject invention is directed to a plant comprising a plant cell transformed to express a polynucleotide encoding a pesticidal agent of the subject invention. Plants of the subject invention include monocots and dicots.

Various pesticidal agents can be used in the compositions of the subject invention. For example, U.S. Pat. Nos. 5,011,909; 5,130,253; and 5,358,934 describe polynucleotides encoding TMOF and functional equivalents thereof. Also, the invention concerns the pesticidal use of NPF peptides, and functional equivalents thereof. Specifically exemplified herein are two NPF peptides which have the following sequences: Ala-Arg-Gly-Pro-Gln-Leu-Arg-Leu-Arg-Phe-$NH_2$ (SEQ ID NO. 1) or Ala-Pro-Ser-Leu-Arg-Leu-Arg-Phe-$NH_2$ (SEQ ID NO. 2).

In one aspect, the pesticides comprise polypeptides, each of which comprises an amino acid sequence having a formula:

$$A^1A^2A^3A^4A^5Fl \qquad \text{(Formula I) (SEQ ID NO. 5)}$$

wherein:

$A^1$ is selected from the group consisting of A, D, F, G, M, P, S and Y;

$A^2$ is selected from the group consisting of A, D, E, F, G, N, P, S and Y;

$A^3$ is optionally present and is selected from the group consisting of A, D, F, G, L P, S and Y;

$A^4$ is optionally present when $A^3$ is present and is selected from the group consisting of A, F, G, L and Y;

$A^5$ is optionally present when $A^4$ is present and is selected from the group consisting of A, F, L and P;

Fl is a flanking region which is optionally present and is selected from the group consisting of: P, PP, PPP, PPPP (SEQ ID NO. 6), and PPPPP (SEQ ID NO. 7).

The peptide preferably does not consist of $YDPAP_6$ (SEQ ID NO. 8), $DYPAP_6$ (SEQ ID NO. 9), $PAP_6$ (SEQ ID NO. 10), YDPAP (SEQ ID NO. 11), $YDPAP_2$ (SEQ ID NO. 12), $YDPAP_3$ (SEQ ID NO. 13), $YDPAP_4$ (SEQ ID NO. 14) or NPTNLH (SEQ ID NO. 15).

In a narrower aspect, the polypeptide comprises an amino acid sequence which consists essentially of the amino acid sequence of Formula I. In a preferred aspect, the polypeptide lacks TMOF amino acids adjacent to the amino acid sequence of Formula I. In still another aspect, the polypeptide consists of the amino acid sequence of Formula I.

In another aspect, only $A^1$, $A^2$, $A^3$, $A^4$ and Fl of Formula I are present. In yet another aspect, only $A^1$, $A^2$, $A^3$ and $A^4$ of Formula I are present. In still a further aspect, only $A^1$, $A^2$, $A^3$ and Fl of Formula I are present. In an additional aspect, only $A^1$, $A^2$ and $A^3$ of Formula I are present. In another aspect, only $A^1$, $A^2$ and Fl of Formula I are present, and in a further aspect, only $A^1$ and $A^2$ of Formula I are present. In a preferred mode, at A and D are present in the amino acid sequence of Formula I and more preferably A, D and Y are present.

One embodiment of the subject invention concerns a peptide having the formula $A^1A^2$ (Formula II) (SEQ ID NO.

63) wherein $A^1$ is an amino acid selected from the group consisting of A, D, F, M, and Y, and $A^2$ is an amino acid selected from the group consisting of A, D, E, P, and Y. In a preferred embodiment, the subject invention is directed to peptides which comprise the amino acids A, D, and Y.

The present invention also comprises various analogs, fragments and derivatives of the forgoing peptides of Formulas I and II (SEQ ID NO. 5 and 63).

The pest control compositions according to the subject invention comprise an NPF or TMOF peptide, or functional equivalent, as a component, or as the sole component. The pest control compositions may further comprise, a carrier solution, compound, or molecule. Pest control compositions of the subject invention also include an NPF or TMOF peptide, or functional equivalent, contained in a cell, virus, plant, or membrane. Examples include, but are not limited to, transformed bacteria, mammalian cells, algae, fungi, yeast viruses, or plants that produce an NPF or TMOF compound.

The term "functional equivalent" as used herein refers to a full length NPF or TMOF peptide, or a fragment or mutant thereof, which has the pest control activity as described and exemplified herein. Functional equivalent would include, for example, an NPF or TMOF peptide in salt, complex, analog, or derivative form. The term "NPF compound" refers to NPF peptides and functional equivalents thereof. The term "TMOF compound" refers to TMOF peptides and functional equivalents thereof.

The pest control compounds of the subject invention may be presented as fusion proteins or peptides, the amino acid sequence of which includes one or more polypeptides of the present invention. In various specific embodiments, two or more of the polypeptides are linked, for example, by peptide bonds between the N-terminus of one portion and the C-terminus of another portion. In other aspects, one or more of the polypeptides can be linked to one or more heterologous peptides or proteins to form pesticidal fusion peptides. Molecules comprising such portions linked by hydrocarbon linkages are also provided. Derivatives of the foregoing fusion proteins are also provided (e.g., branched, cyclized, N- or C-terminal chemically modified, etc.).

In one embodiment, the pesticidal polypeptide comprises a repeating unit of at least 3 amino acids. There may be, for example, from 2 to 10 or more repeating units. Preferably, the repeating unit is connected through at least one amino acid which is cleaved by a pest gut enzyme. As used herein, a pest gut enzyme is an enzyme which is present in the gut of a pest. In a specific embodiment the repeating units are connected through an arginine.

TMOF analogues (5 to 8 amino acids in length, and polymers of these analogues) in which Arg was added at the C-terminus were evaluated to determine their effect on larval growth and development. A series of analogues were synthesized and tested by feeding them to mosquito larvae at concentrations of (0.5 to 5.0 mg/ml; Table 4). Concentrations of 2.0 to 0.065 mg/ml were used to feed mosquito larvae and calculate the Lethal Dose at 50% mortality ($LD_{50}$; Table 4) of the TMOF analogues. Several analogues that were effective at $LC_{50}$ of 0.24 to 0.048 mM were chosen and were injected into $2^{nd}$ instar *Heliothis virescens* and the inhibition of trypsin biosynthesis was followed for 24 hours (Table 5). In both cases larval death and trypsin biosynthesis inhibition was noted (Table 4 and 5). These results indicate that short TMOF analogues or polymers of these analogues with Arg at the termini can be used efficiently to block larval growth by shutting down the enzyme that digests the food in both mosquitoes and Heliothis. The advantage of using short analogues connected by Arg is that they can be digested in the gut into short TMOF analogues that can penetrate the midgut much faster than longer analogues.

NPF and TMOF polypeptides in which only conservative substitutions have been made are also provided by the present invention are also included as peptide derivatives within the scope of the invention. Analogs which have one or more amino acid substitutions forming a branched peptide (e.g., by substitution with an amino acid or amino acid analog having a free amino- or carboxy-side chain that forms a peptide bond with a sequence of one or more amino acids, including but not limited to prolines) or allowing circularization of the peptide (e.g., by substitution with a cysteine, or insertion of a cysteine at the amino- or carboxy-terminus or internally), to provide a sulfhydryl group for disulfide bond formation, are also provided.

Nonclassical amino acids or chemical amino acid analogs can be introduced as a substitution or addition into the NPF and TMOF polypeptides of the present invention. Nonclassical amino acids include but are not limited to the D-isomers of the common amino acids, 2,4-diaminobutyric acid, α-amino isobutyric acid, 4-aminobutyric acid, Abu, 2-amino butyric acid, γ-Abu, ε-Ahx, 6-amino hexanoic acid, Aib, 2-amino isobutyric acid, 3-amino propionic acid, ornithine, norleucine, norvaline, hydroxyproline, sarcosine, citrulline, homocitrulline, cysteic acid, τ-butylglycine, τ-butylalanine, phenylglycine, cyclohexylalanine, β-alanine, fluoro-amino acids, designer amino acids such as β-methyl amino acids, Cα-methyl amino acids, Nα-methyl amino acids, and amino acid analogs in general. Furthermore, the amino acid can be D (dextrorotary) or L (levorotary).

Thus, the NPF and TMOF compounds include peptides containing, as a primary amino acid sequence, all or part of an exemplified polypeptide sequence including altered sequences in which functionally equivalent amino acid residues are substituted for residues within the sequence resulting in a peptide which is functionally active. For example, one or more amino acid residues within the sequence can be substituted by another amino acid of a similar polarity which acts as a functional equivalent, resulting in a silent alteration. Conservative substitutions for an amino acid within the sequence may be selected from other members of the class to which the amino acid belongs (see Table 1). The NPF and TMOF compounds may be made by chemical peptide synthesis or by recombinant production from a nucleic acid encoding the NPF compounds.

The peptides may be presented as fusion proteins or peptides, the amino acid sequence of which includes one or more pesticidal peptides of the present invention. In various specific embodiments, two or more of the pesticidal peptides are linked, for example, by peptide bonds between the N-terminus of one portion and the C-terminus of another portion. In other aspects, one or more of the pesticidal peptides can be linked to one or more heterologous peptides or proteins to form pesticidal fusion peptides. Molecules comprising such portions linked by hydrocarbon linkages are also provided. Derivatives of the foregoing fusion proteins are also provided (e.g., branched, cyclized,—or C-terminal chemically modified, etc.)

Peptides containing the sequences of Formula I, or the NPF peptides, in which only conservative substitutions have been made are also provided by the present invention are also included as peptide derivatives within the scope of the invention. Analogs which have one or more amino acid substitutions forming a branched peptide (e.g., by substitution with an amino acid or amino acid analog having a free amino- or carboxy-side chain that forms a peptide bond with a sequence of one or more amino acids, including but not limited to prolines) or allowing circularization of the peptide; (substitution with a marker, such as antibiotic resistance or fluorescence; appropriate termination sequences; and an operable promoter.

The skilled artisan, having the benefit of the instant description, can use techniques well-known in the art, to transform a host with polynucleotides TMOF and/or NPF compounds. The transformed host then expresses the polynucleotides.

The skilled artisan, having the benefit of the instant description, can use techniques well-known in the art to transform a host with polynucleotides encoding TMOF or the NPF peptides. The transformed host then expresses the polynucleotides.

Plant cells of the subject invention can be produced by known transformation methods routine in the art. Methods of transformation can include use of Agrobacterium, viral vectors, microinjection, PEG, biolistics, and electroporation which are all routinely used to introduce foreign DNA into plant cells. Once in the cell, the foreign DNA is incorporated into the plant genome. In a particular embodiment, the transformation contemplates constructing a vector comprising a regulatory sequence and a polynucleotide which encodes a polypeptide capable of inhibiting trypsin biosynthesis, placing the vector into a selected strain of Agrobacterium, and treating selected plant cells with the Agrobacterium under conditions sufficient to result in transfer of at least some of the vectors from the Agrobacterium to the plant cells, whereby the polynucleotide is expressed in the plant cells. Regulatory sequences can include both promoter and termination sequences.

Possible regulatory sequences can include, but are not limited to, any promoter already shown to be constitutive for expression, such as those of viral origin (CaMV 19S and 35S, TMV, AMV) or so-called "housekeeping" genes (ubiquitin, actin, tubulin) with their corresponding termination/poly A+ sequences. Also, seed-and/or developmentally-specific promoters, such as those from plant fatty acid/lipid biosynthesis genes (acyl carrier proteins, acyltransferases, desaturases, lipid transfer protein genes) or from storage protein genes (zein, napin, cruciferin, conglycinin, or lectin genes, for example), with their corresponding termination/poly A+ sequences can be used for targeted expression. In addition, the gene can be placed under the regulation of inducible promoters and their termination sequences so that gene expression is induced by, for example, light (ribulose biphosphate carboxylase small subunit-3A, chlorophyl A/B binding protein-1), heat (heat shock protein gene promoters) or wounding (mannopine). It is clear to one skilled in the art that a promoter may be used either in native or truncated form, and may be paired with its own or a heterologous termination/polyA+ sequence.

In addition, polypeptides capable of inhibiting trypsin biosynthesis may be localized to specific organelles in the plant cell by ligating DNA encoding peptide leader sequences to the polynucleotide encoding said polypeptide (s). Such leader sequences can be obtained from a variety of known genes of either plant or other origin. These genes encode cytoplasmically-synthesized proteins directed to, for example, mitochondria (the F1-ATPase beta subunit from yeast or tobacco, cytochrome c1 from yeast), chloroplasts (cytochrome oxidase subunit Va from yeast, small subunit of rubisco from pea), endoplasmic reticulum lumen (protein disulfide isomerase), vacuole (carboxypeptidase Y and proteinase A from yeast, phytohemagglutinin from French bean), peroxisomes (D-aminoacid oxidase, uricase) and lysosomes (hydrolases).

A selectable marker for optimum transformation selection can be chosen. Such markers are typically genes which encode for resistance to various toxic chemicals such as antibiotics and herbicides; the resistance is usually conferred by enzymes which typically render the chemical non-toxic. Such toxic chemicals include, for example, hygromycin, kanamycin, methotrexate, and phosphinothricin. Enzymes which confer resistance to these chemicals are hygromycin phosphotransferase, neomycin phosphotransferase, dihydrofolate reductase, and phosphinthricin acetyl transferase. Genes which code for resistance are well known to those of ordinary skill in the art of plant transformation. Plants transformed with such genes are able to grow in the presence of the toxic compound, while non-transformed plants are not. Therefore, such genes serve both as a means of selecting transformed plants and as a marker for transformation, indicating that transformation has occurred.

Plant tissue for use in transformation may be obtained from any suitable plant, i.e., known to be susceptible to transformation by known methods. Appropriate plant tissue includes, but is not limited to, leaves, hypocotyls, cotyledons, stems, callus, single cells, and protoplasts.

In a particular embodiment, transformed callus tissue is selected by growth on selection medium (e.g., medium which contains a toxic chemical and for which the transformed plant contains a resistance gene, by virtue of its transformation). Transformed plants are regenerated and screened for the presence of the biocontrol agent. This involves analyzing tissue by at least one molecular or biological assay to determine which, if any, transformants contain the biocontrol agent polynucleotides. These assays include assays of the tissue for the expression of the resistance gene enzyme, and assays of the tissue for the presence of control agent polynucleotide by, for example, a Southern assay or a PCR assay.

Those plants which are positive for the control agent polynucleotide are grown to maturity, and the expression of the control agent polynucleotide can be determined by analyzing plant tissue for the presence of the polypeptide encoded by the polynucleotide, as for example via a Western blot analysis, and/or for the phenotype of conferred pest resistance as a result of the activity of the control agent.

It is now well known in the art that when synthesizing a gene for improved expression in a host cell, it is desirable to design the gene such that its frequency of codon usage approaches the frequency of preferred codon usage of the host cell. For purposes of the subject invention, "frequency of preferred codon usage" refers to the preference exhibited by a specific host cell in usage of nucleotide codons to specify a given amino acid. To determine the frequency of usage of a particular codon in a gene, the number of occurrences of that codon in the gene is divided by the total number of occurrences of all codons specifying the same amino acid in the gene. Similarly, the frequency of preferred codon usage exhibited by a plant cell can be calculated by averaging frequency of preferred codon usage in a large number of genes expressed by the plant cell. It is preferable that this analysis be limited to genes that are highly expressed by the host cell.

Thus, in one embodiment of the subject invention, plant cells can be genetically engineered, e.g., transformed with genes to attain desired expression levels of the subject proteins. To provide genes having enhanced expression, the DNA sequence of the gene can be modified to comprise codons preferred by highly expressed genes to attain an A+T content in nucleotide base composition which is substantially that found in the transformed host cell. It is also preferable to form an initiation sequence optimal for said plant cell, and to eliminate sequences that cause destabilization, inappropriate polyadenylation, degradation and termination of RNA and to avoid sequences that constitute secondary structure hairpins and RNA splice sites. For example, in synthetic genes, the codons used to specify a given amino acid can be selected with regard to the distribution frequency of codon usage employed in highly expressed genes in the plant cell to specify that amino acid. As is appreciated by those skilled in the art, the distribution frequency of codon usage utilized in the synthetic gene is a determinant of the level of expression.

In yet another embodiment, the subject invention is directed to a method of controlling agricultural and household pests comprising administering a control agent to said pests, wherein said control agent is capable of inhibiting trypsin biosynthesis in said pest.

In a further embodiment, the subject invention is directed to a microbe for producing a biological control agent having the ability to inhibit trypsin biosynthesis in the gut of a pest. Preferably, the microbe is a prokaryotic or eukaryotic cell genetically engineered to express a polynucleotide comprising a nucleotide sequence encoding protein capable of inhibiting trypsin biosynthesis. In a more preferred embodiment, the microbe is a cell that is suitable for feeding pest larvae. Pest larvae synthesize trypsin as their major protease and use the enzyme to digest decaying organic material.

TMOF Receptors and Polynucleotides

In one embodiment, the subject invention is directed to the control of pests using a compound which binds to, or otherwise associates with, a TMOF receptor. Specifically exemplified herein is a TMOF receptor comprising the amino acid sequence shown in SEQ ID NO. 4. Preferably, the polypeptide is encoded by a complete cDNA sequence of a TMOF receptor gene, or fragments or mutants thereof which encode polypeptides having TMOF receptor activity. In a specific embodiment, the TMOF receptor is encoded by a polynucleotide sequence comprising the coding sequence (nucleotides 1–186) shown in SEQ ID NO. 3 or other polynucleotide sequence with codons encoding the amino acid sequence of SEQ ID NO. 4.

Isolated TMOF receptors can be used to produce antibodies according to known techniques. These antibodies may be monoclonal or polyclonal. These antibodies can be used to screen an expression library to identify other clones expressing polypeptides having TMOF receptor activity. Alternatively, these antibodies may be used to identify TMOF receptors from their natural material such as, for example, mosquito or insect gut material.

A specific TMOF receptor sequence is exemplified herein. This sequence is merely exemplary of TMOF receptors. Variant or equivalent receptors (and nucleotide sequences coding for equivalent receptors) having the same or similar TMOF receptor activity can also be utilized. Equivalent receptors will typically have amino acid homology with the exemplified receptor. This amino acid identity will typically be greater than 60%, preferably be greater than 75%, more preferably greater than 80%, more preferably greater than 90%, and can be greater than 95%. These identities are as determined using standard alignment techniques. The amino acid homology will be highest in critical regions of the receptor which account for biological activity or are involved in the determination of three-dimensional configuration which ultimately is responsible for the biological activity. In this regard, certain amino acid substitutions are acceptable and can be expected if these substitutions are in regions which are not critical to activity or are conservative amino acid substitutions which do not affect the three-dimensional configuration of the molecule. For example, amino acids may be placed in the following classes: non-polar, uncharged polar, basic, and acidic. Conservative substitutions whereby an amino acid of one class is replaced with another amino acid of the same type fall within the scope of the subject invention so long as the substitution does not materially alter the biological activity of the compound. Table 1 provides a listing of examples of amino acids belonging to each class.

TABLE 1

| Class of Amino Acid | Examples of Amino Acids |
|---|---|
| Nonpolar | Ala, Val, Leu, Ile, Pro, Met, Phe, Trp |
| Uncharged Polar | Gly, Ser, Thr, Cys, Tyr, Asn, Gln |
| Acidic | Asp, Glu |
| Basic | Lys, Arg, His |

In some instances, non-conservative substitutions can also be made. The critical factor is that these substitutions must not completely diminish the biological activity of the receptor. Further, it is preferable that the conservative substitutions do not significantly detract from the biological activity of the receptor.

The use of polynucleotide probes is well known to those skilled in the art. In one specific example, a cDNA library for mosquito or insect gut cells can be created by routine means, and DNA of interest isolated therefrom. Polynucleotides of the subject invention can be used to hybridize with DNA fragments of the constructed cDNA-library, allowing identification of and selection (or "probing out") of the genes of interest, i.e., those nucleotide sequences which hybridize with the probes of the subject invention and encode polypeptides having TMOF receptor activity. The isolation of these genes can be performed by a person skilled in the art, having the benefit of the instant disclosure, using techniques which are well-known in the molecular biology art.

Thus, it is possible, without the aid of biological analysis, to identify polynucleotide sequences encoding TMOF receptors. Such a probe analysis provides a rapid method for identifying genes encoding TMOF receptors from a wide variety of hosts. The isolated genes can be inserted into appropriate vehicles which can then be used to transform a suitable host.

Various degrees of stringency of hybridization can be employed. The more severe the conditions, the greater the complementarity that is required for duplex formation. Severity of conditions can be controlled by temperature, probe concentration, probe length, ionic strength, time, and the like. Preferably, hybridization is conducted under moderate to high stringency conditions by techniques well known in the art, as described, for example, in Keller, G. H., M. M. Manak (1987) *DNA Probes*, Stockton Press, New York, NY., pp. 169–170.

Examples of various stringency conditions are provided herein. Hybridization of immobilized DNA on Southern blots with 32P-labeled gene-specific probes can be performed by standard methods (Maniatis et al.). In general, hybridization and subsequent washes can be carried out under moderate to high stringency conditions that allow for detection of target sequences with homology to the exemplified polynucleotide sequence. For double-stranded DNA gene probes, hybridization can be carried out overnight at 20–25° C. below the melting temperature (Tm) of the DNA hybrid in 6×SSPE, 5×Denhardt's solution, 0.1% SDS, 0.1 mg/ml denatured DNA. The melting temperature is described by the following formula (Beltz, G. A., K. A. Jacobs, T. H. Eickbush, P. T. Cherbas, and F. C. Kafatos [1983] *Methods of Enzymology*, R. Wu, L. Grossman and K. Moldave [eds.] Academic Press, New York 100:266–285).

Tm=81.5° C.+16.6 Log[Na+]+0.41(%G+C)−0.61 (%formamide)−600/length of duplex in base pairs.

Washes are typically carried out as follows:

(1) Twice at room temperature for 15 minutes in 1×SSPE, 0.1% SDS (low stringency wash).

(2) Once at Tm-20° C. for 15 minutes in 0.2×SSPE, 0.1% SDS (moderate stringency wash).

For oligonucleotide probes, hybridization can be carried out overnight at 10–20° C. below the melting temperature (Tm) of the hybrid in 6×SSPE, 5×Denhardt's solution, 0.1% SDS, 0.1 mg/ml denatured DNA. Tm for oligonucleotide probes can be determined by the following formula:

Tm (° C.)=2(number T/A base pairs)+4(number G/C base pairs) (Suggs, S. V., T. Miyake, E. H. Kawashime, M. J. Johnson, K. Itakura, and R. B. Wallace [1981] *ICN-UCLA Symp. Dev. Biol. Using Purified Genes*, D. D. Brown [ed.], Academic Press, New York, 23:683–693).

Washes can be carried out as follows:

(1) Twice at room temperature for 15 minutes 1×SSPE, 0.1% SDS (low stringency wash).

(2) Once at the hybridization temperature for 15 minutes in 1×SSPE, 0.1% SDS (moderate stringency wash).

In general, salt and/or temperature can be altered to change stringency. With a labeled DNA fragment >70 or so bases in length, the following conditions can be used:

Low: 1 or 2×SSPE, room temperature

Low: 1 or 2×SSPE, 42° C.

Moderate: 0.2× or 1×SSPE, 65° C.

High: 0.1×SSPE, 65° C.

Duplex formation and stability depend on substantial complementarity between the two strands of a hybrid, and, as noted above, a certain degree of mismatch can be tolerated. Therefore, the probe sequences of the subject invention include mutations (both single and multiple), deletions, insertions of the described sequences, and combinations thereof, wherein said mutations, insertions and deletions permit formation of stable hybrids with the target polynucleotide of interest. Mutations, insertions, and deletions can be produced in a given polynucleotide sequence in many ways, and these methods are known to an ordinarily skilled artisan. Other methods may become known in the future.

Identification of Pest Control Compounds

The TMOF receptors can, advantageously, be used to identify pest control compounds. These compounds are those which bind to, or otherwise associate with, the TMOF receptor in a way in which inhibits natural function of the TMOF receptor thereby inhibiting or killing a pest. A person skilled in the art, having the benefit of the instant disclosure, can utilize the TMOF receptors described herein to identify novel pest control compounds. In one embodiment, the TMOF receptor can be purified from its natural sources using, for example, antibodies to the TMOF receptor to obtain the purified protein. This purified protein can then be used to identify compounds which bind to the receptor. Compounds thus identified can then be further evaluated using, for example, appropriate bioassays to confirm and/or characterize the pest control activity of the compound.

As an alternative to purifying TMOF receptors from their natural material, recombinant TMOF receptor protein can be expressed in an appropriate recombinant host which has been transformed with a polynucleotide sequence encoding the TMOF receptor. The polynucleotide sequence used to transform the appropriate host may comprise, for example, the polynucleotide coding sequence disclosed in SEQ ID NO. 3. The host may be transformed so as to express the TMOF receptor at the cell surface or, alternatively, the TMOF receptor may be retained intracellularly or secreted into the surrounding media. In any case, the expressed TMOF receptor may be isolated from the recombinant host using techniques known to those skilled in the art. The recombinant purified protein can then be used as described above to identify compounds which bind to the receptor. As an alternative embodiment, the receptor expressed at the surface of the recombinant cell can be used in conjunction with the whole cell to identify compounds which bind to the receptor.

In another embodiment, TMOF receptors of the subject invention can be applied to a chip or other suitable substrate to facilitate high through put screening of potential pest control compounds.

Once compounds are identified which bind to the TMOF receptor, their pesticidal activity can be confirmed and/or characterized using bioassays known to those skilled in the art. The pesticide compounds of the subject invention can have activity against a variety of pests. These pests include agricultural pests which attack plants as well as pests of animals which attack humans, agricultural animals, and/or domestic animals.

Production of recombinant hosts. The various methods employed in the preparation of the plasmids and transformation of host organisms are well known in the art and are described, for example, in U.S. Pat. Nos. 5,011,909 and 5,130,253. These patents are incorporated herein by reference. These procedures are also described in Maniatis, T., E. F. Fritsch, J. Sambrook (1982) *Molecular Cloning: A Laboratory Manual*, Cold Spring Harbor Laboratory, New York. Thus, it is within the skill of those in the genetic engineering art to extract DNA from microbial cells, perform restrictions enzyme digestions, electrophorese DNA fragments, tail and anneal plasmid and insert DNA, ligate DNA, transform cells, e.g., *E. coli* or plant cells, prepare plasmid DNA, electrophorese proteins, and sequence DNA.

Various markers may be employed for the selection of transformants, including biocide resistance, particularly to antibiotics such as ampicillin, tetracycline, trimethoprim, chloramphenicol, and penicillin; toxins, such as colicin; and heavy metals, such as mercuric salts. Alternatively, complementation providing an essential nutrient to an auxotrophic host may be employed.

The polynucleotide sequences of the subject invention can be introduced directly into the genome of the transformable host cell or can first be incorporated into a vector which is then introduced into the host. Exemplary methods of incorporation include transduction by recombinant phage or cosmids, transfection where specially treated host bacterial cells can be caused to take up naked phage chromosomes, and transformation by calcium precipitation. These methods are well known in the art. Exemplary vectors include plasmids, cosmids, and phages.

It is well known in the art that when synthesizing a gene for improved expression in a host cell it is desirable to design the gene such that its frequency of codon usage approaches the frequency of preferred codon usage of the host cell. For purposes of the subject invention, "frequency of preferred codon usage" refers to the preference exhibited by a specific host cell in usage of nucleotide codons to specify a given amino acid. To determine the frequency of usage of a particular codon in a gene, the number of occurrences of that codon in the gene is divided by the total number of occurrences of all codons specifying the same amino acid in the gene. Similarly, the frequency of preferred codon usage exhibited by a host cell can be calculated by averaging frequency of preferred codon usage in a large number of genes expressed by the host cell. It is preferable that this analysis be limited to genes that are highly expressed by the host cell.

Thus, in one embodiment of the subject invention, cells can be genetically engineered, e.g., transformed with polynucleotides encoding the subject peptides to attain desired expression levels of the subject peptides. To provide genes having enhanced expression, the DNA sequence of the gene can be modified to comprise codons preferred by highly expressed genes to attain an A+T content in nucleotide base composition which is substantially that found in the transformed host cell. It is also preferable to form an initiation sequence optimal for the host cell, and to eliminate sequences that cause destabilization, inappropriate polyadenylation, degradation and termination of RNA and to avoid sequences that constitute secondary structure hairpins and RNA splice sites. For example, in synthetic genes, the codons used to specify a given amino acid can be selected with regard to the distribution frequency of codon usage employed in highly expressed genes in the host cell to specify that amino acid. As is appreciated by those skilled in the art, the distribution frequency of codon usage utilized in the synthetic gene is a determinant of the level of expression.

Assembly of the polynucleotide sequences of this invention can be performed using standard technology known in the art. For example, a structural gene designed for enhanced expression in a host cell can be assembled within a DNA vector from chemically synthesized oligonucleotide duplex segments. Preferably, the DNA vector or construct has an operable promoter and suitable termination signals. The polynucleotide sequence can then be introduced into a host cell and expressed by means known in the art. Preferably, the peptide produced upon expression of the nucleotide sequence is functionally equivalent to the purified peptide. According to the subject invention, "functionally equivalent" refers to retention of function such as, for example, pest control activity.

Furthermore, chimeric toxins may be used according to the subject invention. Methods have been developed for making useful chimeric toxins by combining portions of proteins. The portions which are combined need not, themselves, be pesticidal so long as the combination of portions creates a chimeric protein which is pesticidal. The chimeric toxins may include portions from toxins which do not necessarily act upon the TMOF receptor including, for example, toxins from *Bacillus thuringiensis* (B.t.). B.t. toxins and their various toxin domains are well known to those skilled in the art.

With the teachings provided herein, one skilled in the art could readily produce and use the various toxins and polynucleotide sequences described herein.

The polynucleotide sequences and toxins useful according to the subject invention include not only the exemplified sequences but also fragments of these sequences, variants, mutants, and fusion proteins which retain the characteristic pesticidal activity of the peptides specifically exemplified herein. As used herein, the terms "variants" or "variations" of genes refer to nucleotide sequences which encode the same peptides or which encode equivalent peptides having pesticidal activity. As used herein, the term "equivalent peptides" refers to peptides having the same or essentially the same biological activity against the target pests as the exemplified peptides.

Variations of genes may be readily constructed using standard techniques for making point mutations. Also, fragments of these genes can be made using commercially available exonucleases or endonucleases according to standard procedures. For example, enzymes such as Bal31 or site-directed mutagenesis can be used to systematically cut off nucleotides from the ends of these genes. Also, genes which encode active fragments may be obtained using a variety of restriction enzymes. Proteases may be used to directly obtain active fragments of these peptides.

Polynucleotide sequences encoding the pest control compounds of the subject invention can be introduced into a wide variety of microbial or plant hosts. In the case of toxins, expression of the gene results, directly or indirectly, in the production and maintenance of the pesticide. With suitable microbial hosts, e.g., yeast, chlorella, the microbes can be applied to the situs of the pest, where they will proliferate and be ingested. The result is a control of the pest. Alternatively, the microbe hosting the gene can be killed and treated under conditions that retain and/or prolong the activity of the toxin and stabilize the cell. The treated cell, which retains the toxic activity, then can be applied to the environment of the target pest. In one embodiment, the host is transformed such that the gene encoding the pesticidal peptide is only expressed or maintained for a relatively short period of time, such as days or weeks, so that the material does not persist in the environment.

A wide variety of means are available for introducing a polynucleotide sequence encoding a pesticidal peptide into a microorganism host under conditions which allow for stable maintenance and expression of the gene. These methods are well known to those skilled in the art and are described, for example, in U.S. Pat. No. 5,135,867, which is incorporated herein by reference.

Synthetic genes which encode peptides which are functionally equivalent to the toxins of the subject invention can also be used to transform hosts. Methods for the production of synthetic genes can be found in, for example, U.S. Pat. No. 5,380,831.

Recombinant cells expressing a pest control compound can be treated to prolong the toxin activity and stabilize the cell. The pesticide microcapsule that is formed comprises the toxin within a cellular structure that has been stabilized and protects the toxin when the microcapsule is applied to the environment of the target pest. Suitable host cells include either prokaryotes or eukaryotes. As hosts, of particular interest are the prokaryotes and the lower eukaryotes, such as algae and fungi. The cell will usually be intact and be substantially in the proliferative form when treated, rather than in a spore form.

Treatment of the microbial cell, e.g., a microbe containing the polynucleotide sequence encoding the pesticidal peptide, can be by chemical or physical means, or by a combination of chemical and/or physical means, so long as the technique does not deleteriously affect the properties of the toxin, nor diminish the cellular capability of protecting the toxin. Methods for treatment of microbial cells are disclosed in U.S. Pat. Nos. 4,695,455 and 4,695,462, which are incorporated herein by reference.

Formulations and Administration. As would be appreciated by a person skilled in the art, the pesticidal concentration will vary widely depending upon the nature of the particular formulation, particularly whether it is a concentrate or to be used directly. The pesticide will be present in at least about 0.01% by weight and may be 100% by weight. The dry formulations will have from about 1–95% by weight of the pesticide while the liquid formulations will generally be from about 1–60% by weight of the solids in the liquid phase. The formulations that contain cells will generally have from about 1 to about $10^{10}$ cells/mg. These formulations will be administered at about 50 mg (liquid or dry) to 1 kg or more per hectare.

In applications to the environment of the target pest, the transformant strain can be applied to the natural habitat of the pest. The transformant strain will grow in the pest upon ingestion, while producing the peptide(s) which will have a deleterious effect on the pest. The organism may be applied by pouring, spraying, soaking, injection into the soil, seed coating, seedling coating or spraying, or the like.

In aquatic environments, pest control may be attained at or below the surface by adjusting the specific gravity of the microbe. This can be done by, for example, varying the lipid content of the transformant microorganism strain. It is known that indigenous aquatic algae float due to their lipid content. A variation in lipid content will allow the transformant strain to be distributed at desired depths below the water surface.

In one embodiment, the formulations according to the present invention are formulated to float on the surface of an aqueous medium; in another embodiment, they are formulated to maintain a depth of 0 to 2 feet in an aqueous medium; in yet another embodiment, the formulations are formulated to sink in an aqueous environment.

For commercial formulations, the organisms may be maintained in a nutrient medium which maintains selectivity and results in a low rate of proliferation. Various media may be used, such as yeast extract or L-broth. Once the organism is to be used in the field, the non-proliferating concentrate may be introduced into an appropriate selective nutrient medium, grown to high concentration, generally from about $10^5$ to $10^9$ cells/ml and may then be employed for introduction into the environment of the pest.

All of the U.S. patents cited herein are hereby incorporated by reference.

Following are examples which illustrate procedures for practicing the invention. These examples should not be construed as limiting. All percentages are by weight and all solvent mixture proportions are by volume unless otherwise noted.

EXAMPLE 1

Inhibition of *Spodoptera exigua* by Feeding of TMOF

Individual, first instar larvae *S. exigua* were maintained in separate petri dishes and were fed on artificial diet blocks of 50 mg on which different concentrations of TMOF (0 to 100 μg) were adsorbed. Larvae were fed for 6 days and larval length was measured every 24 hours and compared with controls that were not fed TMOF. Each experiment was repeated 10 times. *S. exigua* larvae that were continuously fed TMOF for 6 days did not grow as fast as the controls (FIG. 1) and maximum inhibition occurred when 100 μg of TMOF was fed with the artificial diet. These results demonstrate that TMOF-like compounds are active in controlling digestion in *S. exigua* as was shown for mosquitoes.

EXAMPLE 2

Effect of TMOF Analogs on Mosquito Larvae

TMOF can traverse the gut epithelium, enter the hemolymph and bind a gut receptor (Borovsky, D. and F. Mahmood (1995) "Feeding the mosquito *Aedes aegypti* with TMOF and its analogs; effect on trypsin biosynthesis and egg development," *Regulatory Peptides* 57:273–281.; Borovsky, D., C. A. Powell, J. K. Nayar, J. E. Blalock, and T. K. Hayes (1994) "Characterization and localization of mosquito-gut receptors for trypsin modulating oostatic factor using complementary peptide immunochemistry" *FASEB J*. 8:350–355.). These results allowed the development of a technique by which TMOF and its analogs could directly be tested. This characteristic permits testing of TMOF and its analogs by feeding them to mosquito and other pest larvae. To determine whether truncated TMOF peptides have an effect on larval growth and development, a series of peptides were synthesized and tested by feeding them to mosquito larvae at concentrations of 0.5 to 5.0 mg/ml (Table 1). Individual, newly hatched *Aedes aegypti* larvae were maintained in separate microtiter wells on a diet of autoclaved yeast (1 mg/ml). The diet was supplemented with TMOF peptides (Table 1). An identical number of larvae which were maintained on yeast served as a control. Larvae that were fed on different concentrations of TMOF peptides (0.5 mg/ml to 5.0 mg/ml) were monitored for eight (8) days for survival and larval growth and development. All control groups survived and larval growth and development was normal. Since larvae swallow only a small portion of the yeast particles that adsorbed the peptides, it is assumed that approximately 1 to 20 ng are taken orally at the high concentrations. These results allowed the calculation of the Lethal Dose at 50% mortality ($LD_{50}$; Table 2) of the TMOF peptides.

TABLE 2

The Effect of TMOF and its analogue peptides on mosquito larvae

| Compound | SEQ ID NO: | N $LD_{50}$ mM ± S.E.M. |
|---|---|---|
| 1. $YDPAP_6$ | 8 | 3 0.2 ± 0.02 |
| 2. $MPDYP_5$ | 29 | 3 > 3.0 |
| 3. YDPAF | 44 | 3 0.33 ± 0.2 |
| 4. YEPAP | 50 | 3 0.35 ± 0.02 |
| 5. FDPAP | 27 | 3 0.37 ± 0.15 |
| 6. YDPLP | 49 | 3 1.5 ± 0.04 |
| 7. YDPAL | 45 | 3 0.52 ± 0.03 |
| 8. YAPAP | 62 | 3 0.54 ± 0.13 |
| 9. YNPAP | 52 | 3 0.55 ± 0.03 |
| 10. (D)YDPAP | 46 | 3 0.56 ± 0.03 |
| 11. YFPAP | 51 | 3 0.64 ± 0.03 |
| 12. YDPAP | 11 | 3 1.64 ± 0.03 |
| 13. YDLAP | 41 | 3 0.6 ± 0.05 |
| 14. YDFAP | 39 | 3 0.74 ± 0.13 |
| 15. YDAAP | 37 | 3 1.0 ± 0.18 |
| 16. YDPGP | 48 | 5 1.1 ± 0.18 |
| 17. Y(D)DPAP | 33 | 3 1.2 ± 0.3 |
| 18. YSPAP | 54 | 3 1.4 ± 0.03 |
| 19. YDPAA | 55 | 3 1.6 ± 0.13 |
| 20. YDPFP | 47 | 4 1.7 ± 0.4 |
| 21. ADPAP | 18 | 4 2.0 ± 0.36 |
| 22. Y(D)DP | 32 | 3 0.28 ± 0.01 |
| 23. DPA | 22 | 3 0.4 ± 0.03 |
| 24. (D)YDP | 43 | 3 0.51 ± 0.05 |

TABLE 2-continued

The Effect of TMOF and its analogue peptides on mosquito larvae

| Compound | SEQ ID NO: | N $LD_{50}$ mM ± S.E.M. |
|---|---|---|
| 25. DAA | 20 | 3 0.91 ± 0.06 |
| 26. YDG | 40 | 3 0.95 ± 0.11 |
| 27. YDF | 38 | 3 0.97 ± 0.11 |
| 28. APA | 19 | 3 1.0 ± 0.07 |
| 29. AAP | 16 | 3 1.08 ± 0.07 |
| 30. YSF | 53 | 3 1.08 ± 0.12 |
| 31. DYP | 24 | 4 1.27 ± 0.17 |
| 32. YDA | 36 | 3 1.6 ± 0.13 |
| 33. FDP | 26 | 3 1.98 ± 0.6 |
| 34. YDP | 42 | 5 2.3 ± 0.4 |
| 35. FSP | 28 | 3 2.3 ± 0.13 |
| 36. YAP | 34 | 3 2.3 ± 0.5 |
| 37. PAA | 30 | 3 2.4 ± 0.34 |
| 38. PAP | 31 | 3 3.17 ± 0.14 |
| 39. FAP | 25 | 3 3.8 ± 0.23 |
| 40. ADP | 17 | 3 > 6.6 |
| 41. YD | 35 | 3 1.24 ± 0.06 |
| 42. DY | 23 | 3 3.0 ± 0.8 |

TABLE 2-continued

The Effect of TMOF and its analogue peptides on mosquito larvae

| Compound | SEQ ID NO: | N $LD_{50}$ mM ± S.E.M. |
|---|---|---|

Groups of 12 to 24 mosquito larvae were incubated with different concentrations of TMOF and its analogue peptides in 100 μl microtiter plates for 7 days. Results are expressed as $LD_{50}$ ± S.E.M.

EXAMPLE 3

Effect of TMOF Analog Peptides on *Heliothis virescens*

Several analogs were chosen and were fed to fourth instar *Heliothis virescens* for seven (7) days and to first instars for fourteen (14) days (Tables 3 and 4). In both cases a reduction in weight gain and trypsin inhibition was noted (Tables 3 and 4).

Individual first instar and fourth instar larvae of *H. virescens* were maintained in separate plastic cups and were fed on artificial diet blocks on which different concentrations of TMOF (0 to 1.6 μg) were adsorbed. Larvae were fed for 5 to 14 days and larval weight and trypsin activity were measured at the end of the experimental periods. Reductions in larval weight and trypsin biosynthesis were observed in fourth instar larvae that were fed TMOF analog peptides for 5 days (see Table 3 analogs 15, 16, and 18). When first instar larvae were fed for 14 days on analogs 15 and 16 (Table 4), an 18% and 26% reduction in weight was observed. These results indicate that the TMOF peptides of the subject invention control trypsin biosynthesis in *H. virescens* as was shown in mosquito and that these TMOF peptides can be used to control these agricultural pest insects.

These results indicate that short TMOF peptides can be used efficiently to block larval growth in mosquitos and other pests. The advantage of using short analogs is that they can penetrate the midgut much faster than longer peptides and are less expensive to synthesize by conventional chemical methods. Synthetic organic mimics of these peptides can also be prepared. These organic compounds can penetrate the larval skin and thus, can be used to spray plants for pest control.

TABLE 3

Effect of TMOF analogs on growth and trypsin biosynthesis on fourth Instar *H. virsecens*

| TMOF analog peptide | SEQ ID NO: | Weight mg ± S.E.M. Start | End | Weight Gain (mg) | Trypsin μg ± S.E.M. | Inhibition (% ± S.E.M.) |
|---|---|---|---|---|---|---|
| Control | | 35.63 ± 1.54 | 219 ± 8.2 | 183.5 | 2.5 ± 0.15 | 0 |
| DYP | 24 | 36.2 ± 2.4 | 216.7 ± 13 | 180.5 | 2.2 ± 0.3 | 14 ± 1.8 |
| YDPGP | 48 | 31.7 ± 1.6 | 199.8 ± 11 | 163.1 | 2.1± 0.1 | 17 ± 1 |
| YDP | 42 | 37 ± 1.5 | 223.4 ± 16 | 186.3 | 2.1 ± 0.3 | 19 ± 3.2 |
| ADAAP | 56 | 35.7 ± 1.5 | 209.7 ± 12 | 174.1 | 2.4 ± 0.3 | 5 ± 0.6 |
| YDAAP | 37 | 38.2 ± 1.3 | 217 ± 9.5 | 179 | 2.1 ± 0.2 | 17 ± 1.6 |
| YDFAP | 39 | 37 ± 1.3 | 201 ± 12 | 164 | 2.1 ± 0.2 | 19 ± 1.5 |
| YSPAP | 54 | 30.6 ± 1.2 | 188 ± 10.6 | 151 | 2.0 ± 0.2 | 19 ± 2 |
| Y(D)DPAP | 33 | 34.6 ± 2 | 188 ± 12 | 153 | 2.1 ± 0.2 | 15 ± 1.3 |

Fourth instar larvae were weighed and fed on synthetic food and 0.8 mg of TMOF analogs for 5 days. After feeding, larvae were weighed and guts were removed and groups of 3 to 4 guts were incubated with [$^3$H]DFP and analyzed for trypsin biosynthesis. Results are average of 3 to 10 experiments ± S.E.M.

TABLE 4

Feeding of *H. virescens* on TMOF analogs for 14 days

| TMOF analog | SEQ ID NO: | N | Number of Dead Larvae | Weight (mg) ± S.E.M. | Weight Reduction (%) ± S.E.M. |
|---|---|---|---|---|---|
| Control | | 8 | 2 | 163 ± 12 | 0 |
| DYP | 24 | 9 | 1 | 149 ± 9 | 9 ± 0.5 |
| YDPGP | 48 | 8 | 2 | 153 ± 10 | 6 ± 0.4 |
| YDP | 42 | 9 | 0 | 157 ± 10 | 4 ± 0.2 |
| ADAAP | 56 | 10 | 0 | 141 ± 9 | 7 ± 0.4 |
| YDAAP | 37 | 10 | 0 | 133 ± 7 | 18 ± 1 |
| YDFAP | 39 | 9 | 1 | 121 ± 7 | 26 ± 1.5 |
| YSPAP | 54 | 10 | 0 | 168 ± 11 | 0 |
| Y(D)DPAP | 33 | 9 | 1 | 152 ± 27 | 7 ± 1 |

First instar larvae were fed individually 1.6 mg of TMOF analogs for 14 days. After feeding, the weight of each larvae was determined and expressed as an average of 9 to 10 determinations ± S.E.M.

EXAMPLE 4

Biological Activity of Compounds Which Bind to TMOF Receptors

Control agents which bind with TMOF receptors can be tested to confirm and characterize pest control activity. Many bioassays are known to those skilled in the art for the purpose of evaluating pesticidal activity. Assays for evaluating mosquito control activity are known to those skilled in the art and are described in, for example, U.S. Pat. No. 5,436,002. Bioassays for evaluating the pest control activity against other targets are also known to those skilled in the art and are described in, for example, U.S. Pat. Nos. 5,596,071; 5,188,960; and 5,366,892.

EXAMPLE 5

Bioassays for Activity Against Lepidopteron and Coleopterans

Biological activity of the control compounds of the subject invention can be confirmed using standard bioassay procedures. One such assay is the budworm-bollworm (*Heliothis virescens* [Fabricius] and *Helicoverpa zea* [Boddie]) assay. Lepidoptera bioassays can be conducted with either surface application to artificial insect diet or diet incorporation of samples. All Lepidopteran insects can be tested from the neonate stage to the second instar. All assays can be conducted with either toasted soy flour artificial diet or black cutworm artificial diet (BioServ, Frenchtown, N.J.).

Diet incorporation can be conducted by mixing the samples with artificial diet at a rate of 6 mL suspension plus 54 mL diet. After vortexing, this mixture is poured into plastic trays with compartmentalized 3-ml wells (Nutrend Container Corporation, Jacksonville, Fla.). A water blank containing no control compound serves as the control. First instar larvae (USDA-ARS, Stoneville, Miss.) are placed onto the diet mixture. Wells are then sealed with Mylar sheeting (ClearLam Packaging, IL) using a tacking iron, and several pinholes are made in each well to provide gas exchange. Larvae were held at 25° C. for 6 days in a 14:10 (light:dark) holding room. Mortality and stunting are recorded after six days.

Bioassay by the top load method utilizes the same sample and diet preparations as listed above. The samples are applied to the surface of the insect diet. In a specific embodiment, surface area can range from 0.3 to approximately 0.8 $cm^2$ depending on the tray size. In one embodiment, 96 well tissue culture plates can be used. Following application, samples are allowed to air dry before insect infestation. A water blank containing no control compound can serve as the control. Eggs are then applied to each treated well and are then sealed with Mylar sheeting (ClearLam Packaging, IL) using a tacking iron, and pinholes are made in each well to provide gas exchange. Bioassays are held at 25° C. for 7 days in a 14:10 (light:dark) or 28° C. for 4 days in a 14:10 (light:dark) holding room. Mortality and insect stunting are recorded at the end of each bioassay.

Another assay useful according to the subject invention is the Western corn rootworm assay. Samples can be bioassayed against neonate western corn rootworm larvae (*Diabrotica virgifera virgifera*) via top-loading of sample onto an agar-based artificial diet at a rate of 160 $mi/cm^2$. Artificial diet can be dispensed into 0.78 $cm^2$ wells in 48-well tissue culture or similar plates and allowed to harden. After the diet solidifies, samples are dispensed by pipette onto the diet surface. Excess liquid is then evaporated from the surface prior to transferring approximately three neonate larvae per well onto the diet surface by camel's hair brush. To prevent insect escape while allowing gas exchange, wells are heat-sealed with 2-mil punched polyester film with 27HT adhesive (Oliver Products Company, Grand Rapids, Mich.). Bioassays are held in darkness at 25° C., and mortality scored after four days.

Analogous bioassays can be performed by those skilled in the art to assess activity against other pests, such as the black cutworm (*Agrotis ipsilon*).

EXAMPLE 6

Injecting TMOF-r Analogues Into *Heliothis virescens*

Individual second instar larvae of *H. virescens* were injected with TMOF-R analogues (10 to 0.25 μg per larva) and maintained in separate plastic cups on artificial diet. Twenty-four hours after the injections 3 groups of larvae (3 per group) were assayed for trypsin biosynthesis using BApNA (trypsin specific substrate; Table 5).

TABLE 5

Effect of TMOF-R analogues on trypsin biosynthesis in *Heliothis virescens*

| Compound | SEQ ID NO: | N | Amount (μg/injections) | Inhibition (% ± S.E.M.) |
|---|---|---|---|---|
| 1. $YDPAP_6$ | 8 | 3 | 10 | 56 ± 26 |
| 2. $YDPAP_6$ | 8 | 3 | 1 | 25 ± 2 |
| 3. $YDPAP_6$ | 8 | 3 | 0.5 | 11 ± 1 |
| 4. $YDPAP_6$ | 8 | 3 | 0.25 | 19.5 ± 0.7 |
| 5. YDPAPR | 57 | 3 | 10 | 53 ± 25 |
| 6. YDPAPR | 57 | 3 | 1 | 31.5 ± 2 |
| 7. YDPAPR | 57 | 3 | 0.5 | 14 ± 1 |
| 8. YDPAPR | 57 | 3 | 0.25 | 11 ± 1 |
| 9. YDPAFR | 58 | 3 | 10 | 0 ± 0 |
| 10. YDPAR | 59 | 3 | 10 | 33.5 ± 9 |
| 11. YDPAR | 59 | 3 | 1 | 39 ± 2 |
| 12. YDPAR | 59 | 3 | 0.5 | 1 ± 0.07 |
| 13. DPAR | 60 | 3 | 10 | 100 |
| 14. DPAR | 60 | 3 | 1 | 17 ± 2 |
| 15. $(DPAR)_4$ | 61 | 3 | 10 | 58 ± 36 |
| 16. $(DPAR)_4$ | 61 | 3 | 1 | 35 ± 7 |
| 17. $(DPAR)_4$ | 61 | 3 | 0.5 | 3 ± 0.3 |

Groups of *H. virescens* were injected with TMOF-R analogues in 0.5 μl of Sterile water and 24 hours later trypsin biosynthesis was followed using BApNA. Results were compared to controls that were injected with sterile distilled water and are expressed as an average of 3 determination ± S.E.M>

Trypsin biosynthesis was clearly inhibited 24 hours after injecting the TMOF-R analogues (Table 5). DPAR (SEQ ID NO. 60) at 10 μg inhibited 75% of trypsin biosynthesis, whereas TMOF caused 56% inhibition. These results indicate that TMOF-like compounds control trypsin biosynthesis in *H. virescens* as was shown in mosquito, and that these analogues can be used to control these agricultural pests.

EXAMPLE 7

Target Pests

Toxins of the subject invention can be used, alone or in combination with other toxins, to control one or more non-mammalian pests. These pests may be, for example, those listed in Table 6. Activity can readily be confirmed using the bioassays provided herein, adaptations of these bioassays, and/or other bioassays well known to those skilled in the art.

TABLE 6

Example of Target pest species

| ORDER/Common Name | Latin Name |
|---|---|
| LEPIDOPTERA | |
| European Corn Borer | *Ostrinia nubilalis* |
| European Corn Borer resistant to Cry1A | *Ostrinia nubilalis* |
| Black Cutworm | *Agrotis ipsilon* |
| Fall Armyworm | *Spodoptera frugiperda* |
| Southwestern Corn Borer | *Diatraea grandiosella* |
| Corn Earworm/Bollworm | *Helicoverpa zea* |
| Tobacco Budworm | *Heliothis virescens* |
| Tobacco Budworm Rs | *Heliothis virescens* |
| Sunflower Head Moth | *Homeosoma ellectellum* |
| Banded Sunflower Moth | *Cochylis hospes* |
| Argentine Looper | *Rachiplusia nu* |
| Cabbage Looper | *Trichophria ni* |
| Spilosoma | *Spilosoma virginica* |
| Bertha Armyworm | *Mamestra configurata* |
| Diamondback Moth | *Plutella xylostells* |
| COLEOPTERA | |
| Red Sunflower Seed Weevil | *Smicronyx fulvus* |
| Sunflower Stem Weevil | *Cylindrocopturus adspersus* |
| Sunflower Beetle | *Zygoramma exclamationis* |
| Canola Flea Beetle | *Phyllotreta cruciferae* |
| Western Corn Rootworm | *Diabrotica virgifera virgifera* |
| DIPTEPA | |
| Hessian Fly | *Mayetiola destructor* |
| HOMOPTERA | |
| Greenbug | *Schizaphis graminum* |
| HEMIPTERA | |
| Lygus Bug | *Lygus lineolaris* |
| NEMATODA | *Heterodera glycines* |

EXAMPLE 8

Insertion of Toxin Genes Into Plants

One aspect of the subject invention is the transformation of plants with genes encoding the insecticidal toxin of the present invention. The transformed plants are resistant to attack by the target pest.

Genes encoding pesticidal toxins, as disclosed herein, can be inserted into plant cells using a variety of techniques which are well known in the art. For example, a large number of cloning vectors comprising a replication system in *E. coli* and a marker that permits selection of the transformed cells are available for preparation for the insertion of foreign genes into higher plants. The vectors comprise, for example, pBR322, pUC series, M13mp series, pACYC184, etc. Accordingly, the sequence encoding the Bacillus toxin can be inserted into the vector at a suitable restriction site. The resulting plasmid is used for transformation into *E. coli*. The *E. coli* cells are cultivated in a suitable nutrient medium, then harvested and lysed. The plasmid is recovered. Sequence analysis, restriction analysis, electrophoresis, and other biochemical-molecular biological methods are generally carried out as methods of analysis. After each manipulation, the DNA sequence used can be cleaved and joined to the next DNA sequence. Each plasmid sequence can be cloned in the same or other plasmids. Depending on the method of inserting desired genes into the plant, other DNA sequences may be necessary. If, for example, the Ti or Ri plasmid is used for the transformation of the plant cell, then at least the right border, but often the right and the left border of the Ti or Ri plasmid T-DNA, has to be joined as the flanking region of the genes to be inserted.

The use of T-DNA for the transformation of plant cells has been intensively researched and sufficiently described in EP 120 516; Hoekema (1985) In: *The Binary Plant Vector System*, Offset-durkkerij Kanters B. V., Alblasserdam, Chapter 5; Fraley et al., *Crit. Rev. Plant Sci.* 4:1–46; and An et al. (1985) *EMBO J.* 4:277–287.

Once the inserted DNA has been integrated in the genome, it is relatively stable there and, as a rule, does not come out again. It normally contains a selection marker that confers on the transformed plant cells resistance to a biocide or an antibiotic, such as kanamycin, G418, bleomycin, hygromycin, or chloramphenicol, inter alia. The individually employed marker should accordingly permit the selection of transformed cells rather than cells that do not contain the inserted DNA.

A large number of techniques are available for inserting DNA into a plant host cell. Those techniques include transformation with T-DNA using *Agrobacterium tumefaciens* or *Agrobacterium rhizogenes* as transformation agent, fusion, injection, biolistics (microparticle bombardment), or electroporation as well as other possible methods.

One of the most widely used approaches for the introduction of DNA into plant cells exploits the natural DNA-transferring properties of *Agrobacterium tumefacients* and *Agrobacterium rhizogenes*, the two species which cause crown gall and hairy root. Their ability to cause disease depends on the presence of large plasmids, in excess of 100 kb, which are referred to as the "Tumour-inducing" or (Ti) and "Root-inducing" (or Ri) plasmids respectively.

A region referred to as the T-DNA ("Transferred DNA") is transferred from an infecting Agrobacterium cell into the nucleus of the plant cell, where it is integrated into the plant genome. Transfer of the T-DNA depends on a set of genes called vir if they are on the Ti plasmid, or chv if they are on the chromosome. These genes are induced in response to various compounds in exudates from wounded plants. The T-DNA itself is flanked by repeated sequences of around 25 base pairs, called border repeats (or left and right borders). The T-DNA contains a group of genes referred to as the onc genes, which are responsible for the oncogenicity of the T-DNA.

The use of Agrobacterium in the genetic manipulation of plants involves the insertion of foreign DNA into the T-DNA of a bacterial cell and subsequent transfer of the DNA by the transformed bacterium into the plant. As long as the necessary proteins are provided by the bacterium, any sequences flanked by the T-DNA border repeats can be transferred into the recipient plant cell genome. The Ti plasmids are too large to manipulate directly, but this problem can be circumvented by using cointegrative and binary systems.

The two main components of a cointegrative system are a Ti plasmid that has typically been modified by the replacement of material between the border repeats (including the onc sequences) by pBR322; and a intermediate vector, which is a modified pBR322 containing an extra marker, such as kanamycin resistance. The gene to be introduced into the target plant is first cloned in to the intermediate vector, and this construct is then introduced into Agrobacterium containing the Ti vector. The pBR322-based plasmid cannot replicate efficiently inside Agrobacterium, so selection for kanamycin resistance identifies those Agrobacterium cells where the pBR322-based intermediate plasmid has been integrated by homologous recombination into the Ti plasmid. Because the recombination is homologous, it will take place across the pBR322 sequences and therefore result in integration between the border repeats.

The need for cointegration of the plasmids can be circumvented by use of a binary vector, such as pBin19, a small plasmid containing a pair of left and right borders. The lacZ region, located within the borders, facilitates insertion and detection of DNA. A neomycin phosphotransferase gene, typically modified for expression in plants by addition of nopalline synthase expression sequences, is also present within the borders. Outside the left and right borders, there is typically a kanamycin resistance gene that will function in prokaryotes and a broad host-range origin derived from the plasmid pRK252. The proteins that catalyze transfer of the T-DNA into the host plant do not have to be cis-encoded (i.e., do not have to be encoded by the same molecule). Therefore, if the binary vector in introduced into Agrobacterium that already contains a resident Ti plasmid, the resident plasmid can provide all the functions needed to transfer into a plant nucleus the DNA between the borders of the binary vector.

If Agrobacteria are used for the transformation, the DNA to be inserted has to be cloned into special plasmids, namely either into an intermediate vector or into a binary vector. The intermediate vectors can be integrated into the Ti or Ri plasmid by homologous recombination owing to sequences that are homologous to sequences in the T-DNA. The Ti or Ri plasmid also comprises the vir region necessary for the transfer of the T-DNA. Intermediate vectors cannot replicate themselves in Agrobacteria. The intermediate vector can be transferred into *Agrobacterium tumefaciens* by means of a helper plasmid (conjugation). Binary vectors can replicate themselves both in *E. coli* and in Agrobacteria. They comprise a selection marker gene and a linker or polylinker which are framed by the right and left T-DNA border regions. They can be transformed directly into Agrobacteria (Holsters et al. [1978] *Mol. Gen. Genet*. 163:181–187). The Agrobacterium used as host cell is to comprise a plasmid carrying a vir region. The vir region is necessary for the transfer of the T-DNA into the plant cell. Additional T-DNA may be contained. The bacterium so transformed is used for the transformation of plant cells. Plant explants can advantageously be cultivated with *Agrobacterium tumefaciens* or *Agrobacterium rhizogenes* for the transfer of the DNA into the plant cell. Whole plants can then be regenerated from the infected plant material (for example, pieces of leaf, segments of stalk, roots, but also protoplasts or suspension-cultivated cells) in a suitable mediun, which may contain antibiotics or biocides for selection. The plants so obtained can then be tested for the presence of the inserted DNA. No special demands are made of the plasmids in the case of injection and electroporation. It is possible to use ordinary plasmids, such as, for example, pUC derivatives. In biolistic transformation, plasmid DNA or linear DNA can be employed.

The transformed cells are regenerated into morphologically normal plants in the usual manner. If a transformation event involves a germ line cell, then the inserted DNA and corresponding phenotypic trait(s) will be transmitted to progeny plants. Such plants can be grown in the normal manner and crossed with plants that have the same transformed hereditary factors or other hereditary factors. The resulting hybrid individuals have the corresponding phenotypic properties.

In a preferred embodiment of the subject invention, plants will be transformed with genes wherein the codon usage has been optimized for plants. See, for example, U.S. Pat. No. 5,380,831. Also, advantageously, plants encoding a truncated toxin will be used. The truncated toxin typically will encode about 55% to about 80% of the full length toxin. Methods for creating synthetic Bacillus genes for use in plants are known in the art.

EXAMPLE 9

Construction of Vector and Transfer to Agrobacterium

Vectors are constructed in which the TMOF gene is placed under the control of different promoters and followed by different termination/poly adenylation sequences. The vector used for transformation contains both the desired selectable marker and the TMOF gene expression cassette. TMOF cDNA can be subcloned into a binary expression vector such as pGA643 (An, Gynheung, Paul R. Ebert, Amitava Mitra, Sam B. Ha [1988] *Plant Molecular Biology Manual* A3-1-19). The binary vector is then mobilized into *Agrobacterium tumefaciens* LBA4404 by triparental mating (An et al., supra). Transformed Agrobacterium is selected for streptomycin, kanamycin, and tetracycline resistance. Sugarbeet cultivar kwerta is propagated in vitro as shoot cultures in MS medium (Marashige, T. and F. Skoog [1962] *Physiol. Plant* 15:473–497) supplemented with 30 g/l sucrose and 0.25 mg/l BAP (Lindsey, K. and P. Gallois [1990] *J. Exp. Bot*. 41:529–536), under continuous light.

The plasmid described above is introduced into a suitable Agrobacterium strain according to routine techniques. See Rogers, S. G. et al. (1988) *Plant Molecular Biology Manual A*2 (Kluner Academic Publishers, Dordrecht), pp. 1–12.

EXAMPLE 10

Transformation of Sugarbeet

For transformation, shoot base explants are derived from the axenic shoot cultures of sugarbeet. The explants are incubated in a suspension of the Agrobacterium ($2.5\times10^8$ cells/ml) described above and cultured on selection medium (MS medium supplemented with BAP 1 mg/l, carbonicillin 200 mg/l, kanamycin 100 mg/l and 5 $\mu$M glycine hetarine).

The tissue slices are transferred to fresh selection medium every fifteen days. Putative transgenic shoots identified by kanarnycin-resistance are then transferred to cooking medium (MS medium supplemented with NAA 5 mg/l). Plants are regenerated.

It should be understood that the examples and embodiments described herein are for illustrative purposes only and that various modifications or changes in light thereof will be suggested to persons skilled in the art and are to be included within the spirit and purview of this application and the scope of the appended claims.

What is claimed is:

1. A method for controlling a plant pest wherein said method comprise contacting said pest with a pesticidally effective amount of a composition comprising a pesticidal polypeptide that comprises amino acid residues: Ala, Asp, and Tyr having at least one of the following two characteristics:

I) said polypeptide is a trypsin modulating oostatic factor (TMOF) compound; and II) said polypeptide binds to a TMOF receptor;

wherein said pesticidal polypeptide inhibits trypsin biosynthesis within said pest, and wherein said pesticidal polypeptide does not consist of a polypeptides selected from the group consisting of SEQ ID NO: 8, SEQ ID NO: 9, SEQ ID NO: 10, SEQ ID NO: 11, SEQ ID NO: 12, SEQ ID NO: 13, SEQ ID NO: 14, and SEQ ID NO: 15.

2. The method, according to claim 1, wherein said pesticidal polypeptide consist of from 2 to 5 amino acids.

3. The method, according to claim 1, wherein the C-terminal residue of said pesticidal polypeptide is an arginine.

4. The method, according to claim 1 wherein said pesticidal polypeptide comprises SEQ ID NO:61.

5. The method, according to claim 1, wherein said TMOF receptor comprises SEQ ID NO: 4.

6. A method for controlling a plant pest wherein said method comprises contacting said pest with a pesticidally effective amount of a composition comprising a pesticidal polypeptide that comprises amino acid residues: Ala, Asp, and Tyr having at least one of the following two characteristics:

I) said polypeptide us a trypsin modulating oostatic factor (TMOF) compound; and II) said polypeptide binds to a TMOF receptors;

wherein said pesticidal polypeptide inhibits trypsin biosynthesis within said pest, wherein said pesticidal polypeptide consists of from 5 and 8 amino acids, and wherein said pesticidal polypeptide does not consist of a polypeptide selected from the group consisting of SEQ ID NO: 8, SEQ ID NO: 9, SEQ ID NO: 10, SEQ ID NO: 11, SEQ ID NO: 12, SEQ ID NO:13, SEQ ID NO: 14, and SEQ ID NO: 15.

7. A method for controlling a plant pest wherein said method comprises contacting said pest with a pesticidally effective amount of a composition comprising a pesticidal polypeptide that comprises amino acid residues: Ala, Asp, and Tyr having at least one of the following two characteristic:

I) said polypeptide is a trypsin modulating oostatic factor (TMOF) compound; and II) said polypeptide binds to a TMOF receptor;

wherein said pesticidal polypeptide inhibits trypsin biosynthesis within said pest, wherein said pesticidal polypeptide comprises a repeating amino acid sequence, and wherein said repeating amino acid sequence is at least 3 amino acids in length and the repeating sequence is connected through an amino acid residue that is specifically cleaved by proteolytic enzyme.

8. The method, according to claim 7, wherein said pesticidal polypeptide does not consist of a polypeptide selected from the group consisting of SEQ ID NO: 8, SEQ ID NO: 9, SEQ ID NO: 10, SEQ ID NO: 11, SEQ ID NO: 12, SEQ ID NO:13, SEQ ID NO: 14, and SEQ ID NO: 15.

9. The method, according to claim 7, wherein said pesticidal polypeptide comprises 2 and 10 repeats of said repeating amino acid sequence.

10. A method for controlling a plant pest wherein said method comprises contacting said pest with a pesticidally effective amount of a composition comprising a pesticidal polypeptide that comprises amino acids Ala, Asp, and Ty having at least one of the following two characteristic:

I) said polypeptide is a trypsin modulating oostatic factor (TMOF) compound; and II) said polypeptide binds to a TMOF receptor;

wherein said pesticidal polypeptide inhibits trypsin biosynthesis within said pest, wherein said pesticidal polypeptide comprising a repeating amino acid sequence, and wherein said repeating amino acid sequence is 5 to 8 amino acids in length and the repeating sequence is connected through amino acid residue that is specifically cleaved by proteolytic enzyme and the repeating sequence is connected through an arginine.

11. The method, according to claim 10, wherein said pesticidal polypeptide does not consist of a polypeptide selected from the group consisting of SEQ ID NO: 8, SEQ ID NO: 9, SEQ ID NO: 10, SEQ ID NO: 11, SEQ ID NO: 12, SEQ ID NO:13, SEQ ID NO: 14, and SEQ ID NO: 15.

12. The method, according to claim 10, wherein said pesticidal polypeptide comprises 2 to 10 repeats of the repeating amino acid sequence.

* * * * *

UNITED STATES PATENT AND TRADEMARK OFFICE

CERTIFICATE OF CORRECTION

PATENT NO. : 6,635,265 B1
DATED : October 21, 2003
INVENTOR(S) : Borovsky

It is certified that error appears in the above-identified patent and that said Letters Patent is hereby corrected as shown below:

Column 4,
Line 46, "are no present" should read -- are not present --

Column 23,
Line 63, "160 mi/$cm^2$" should read -- 160 ml/$cm^2$ --

Column 28,
Line 57, "kanarnycin" should read -- kanamycin --

Column 51,
Line 33, "method comprise" should read -- method comprises --
Line 43, "of a polypeptides" should read -- of a polypeptide --
Line 48, "polypeptide consist" should read -- polypeptide consists --
Line 62, "polypeptide us a" should read -- polypeptide is a --
Line 67, "5 and 8" should read -- 5 to 8 --

Column 52,
Line 57, "2 and 10" should read -- 2 to 10 --
Line 62, "and Ty" should read -- and Tyr --
Line 63, "two characteristic:" should read -- two characteristics: --

Column 53,
Line 1, "comprising a" should read -- comprises a --
Lines 3-4, "through amino acid" should read -- through an amino acid --

Signed and Sealed this

Fifteenth Day of June, 2004

JON W. DUDAS
*Acting Director of the United States Patent and Trademark Office*

SEQUENCE LISTING

```
<160> NUMBER OF SEQ ID NOS: 63

<210> SEQ ID NO 1
<211> LENGTH: 10
<212> TYPE: PRT
<213> ORGANISM: Leptinotarsa decemlineata

<400> SEQUENCE: 1

Ala Arg Gly Pro Gln Leu Arg Leu Arg Phe
1               5                   10


<210> SEQ ID NO 2
<211> LENGTH: 8
<212> TYPE: PRT
<213> ORGANISM: Leptinotarsa decemlineata

<400> SEQUENCE: 2

Ala Pro Ser Leu Arg Leu Arg Phe
1               5


<210> SEQ ID NO 3
<211> LENGTH: 378
<212> TYPE: DNA
<213> ORGANISM: Aedes aegypti
<220> FEATURE:
<221> NAME/KEY: CDS
<222> LOCATION: (1)..(189)
<223> OTHER INFORMATION:

<400> SEQUENCE: 3

ata ctg ggg agg ggg ggg ggg gac att ggg tta ctc agt tca gac caa       48
Ile Leu Gly Arg Gly Gly Gly Asp Ile Gly Leu Leu Ser Ser Asp Gln
1               5                   10                  15

agg agt ttc agc act gaa act ctg ctt aaa gaa cta aaa aga gaa gcg       96
Arg Ser Phe Ser Thr Glu Thr Leu Leu Lys Glu Leu Lys Arg Glu Ala
            20                  25                  30

gcg gct gag gag cgg agt gct gcc tcc aac tcg ggg tcg gtg gtt ccc      144
Ala Ala Glu Glu Arg Ser Ala Ala Ser Asn Ser Gly Ser Val Val Pro
        35                  40                  45

ctc tcg gag caa agg ctg atg gga cat ctg gcg gcc gcg ctg tga          189
Leu Ser Glu Gln Arg Leu Met Gly His Leu Ala Ala Ala Leu
    50                  55                  60

gccggctttc ctgctgccac tttgggcgcc ttggatggag atcccaattg cagtttgtat    249

tttatttttt tataagggac acgtggaaaa accaaaccaa accaaacaaa gccaacaaac    309

cacgacggtc cttattttaa acctcagact ccataaagaa acctttctat ccaaaaaaaa    369

aaaaaaaaa                                                            378


<210> SEQ ID NO 4
<211> LENGTH: 62
<212> TYPE: PRT
<213> ORGANISM: Aedes aegypti

<400> SEQUENCE: 4

Ile Leu Gly Arg Gly Gly Gly Asp Ile Gly Leu Leu Ser Ser Asp Gln
1               5                   10                  15

Arg Ser Phe Ser Thr Glu Thr Leu Leu Lys Glu Leu Lys Arg Glu Ala
            20                  25                  30

Ala Ala Glu Glu Arg Ser Ala Ala Ser Asn Ser Gly Ser Val Val Pro
        35                  40                  45
```

-continued

```
Leu Ser Glu Gln Arg Leu Met Gly His Leu Ala Ala Ala Leu
    50                  55                  60


<210> SEQ ID NO 5
<211> LENGTH: 10
<212> TYPE: PRT
<213> ORGANISM: Artificial Sequence
<220> FEATURE:
<223> OTHER INFORMATION: TMOF peptide
<220> FEATURE:
<221> NAME/KEY: MISC_FEATURE
<222> LOCATION: (1)..(1)
<223> OTHER INFORMATION: Can be Ala, Asp, Phe, Gly, Met, Pro, Ser, or
      Tyr.
<220> FEATURE:
<221> NAME/KEY: MISC_FEATURE
<222> LOCATION: (2)..(2)
<223> OTHER INFORMATION: Can be Ala, Asp, Glu, Phe, Gly, Asn, Pro, Ser,
      or Tyr.
<220> FEATURE:
<221> NAME/KEY: MISC_FEATURE
<222> LOCATION: (3)..(3)
<223> OTHER INFORMATION: Can be Ala, Asp, Phe, Gly, Leu, Pro, Ser, or
      Tyr.
<220> FEATURE:
<221> NAME/KEY: MISC_FEATURE
<222> LOCATION: (4)..(4)
<223> OTHER INFORMATION: Is optionally present and can be Ala, Phe, Gly,
      Leu, or Tyr.
<220> FEATURE:
<221> NAME/KEY: MISC_FEATURE
<222> LOCATION: (5)..(5)
<223> OTHER INFORMATION: Is optionally present and can be Ala, Phe, Leu,
      or Pro.
<220> FEATURE:
<221> NAME/KEY: MISC_FEATURE
<222> LOCATION: (6)..(10)
<223> OTHER INFORMATION: Each of amino acids 6-10 are optionally
      present.

<400> SEQUENCE: 5

Xaa Xaa Xaa Xaa Xaa Pro Pro Pro Pro Pro
1               5                   10


<210> SEQ ID NO 6
<211> LENGTH: 4
<212> TYPE: PRT
<213> ORGANISM: Artificial Sequence
<220> FEATURE:
<223> OTHER INFORMATION: Flanking region

<400> SEQUENCE: 6

Pro Pro Pro Pro
1


<210> SEQ ID NO 7
<211> LENGTH: 5
<212> TYPE: PRT
<213> ORGANISM: Artificial Sequence
<220> FEATURE:
<223> OTHER INFORMATION: Flanking region

<400> SEQUENCE: 7

Pro Pro Pro Pro Pro
1               5


<210> SEQ ID NO 8
<211> LENGTH: 10
<212> TYPE: PRT
<213> ORGANISM: Aedes aegypti

<400> SEQUENCE: 8
```

-continued

```
Tyr Asp Pro Ala Pro Pro Pro Pro Pro Pro
1               5                   10


<210> SEQ ID NO 9
<211> LENGTH: 10
<212> TYPE: PRT
<213> ORGANISM: Artificial Sequence
<220> FEATURE:
<223> OTHER INFORMATION: TMOF peptide

<400> SEQUENCE: 9

Asp Tyr Pro Ala Pro Pro Pro Pro Pro Pro
1               5                   10


<210> SEQ ID NO 10
<211> LENGTH: 8
<212> TYPE: PRT
<213> ORGANISM: Artificial Sequence
<220> FEATURE:
<223> OTHER INFORMATION: TMOF peptide

<400> SEQUENCE: 10

Pro Ala Pro Pro Pro Pro Pro Pro
1               5


<210> SEQ ID NO 11
<211> LENGTH: 5
<212> TYPE: PRT
<213> ORGANISM: Artificial Sequence
<220> FEATURE:
<223> OTHER INFORMATION: TMOF peptide

<400> SEQUENCE: 11

Tyr Asp Pro Ala Pro
1               5


<210> SEQ ID NO 12
<211> LENGTH: 6
<212> TYPE: PRT
<213> ORGANISM: Artificial Sequence
<220> FEATURE:
<223> OTHER INFORMATION: TMOF peptide

<400> SEQUENCE: 12

Tyr Asp Pro Ala Pro Pro
1               5


<210> SEQ ID NO 13
<211> LENGTH: 7
<212> TYPE: PRT
<213> ORGANISM: Artificial Sequence
<220> FEATURE:
<223> OTHER INFORMATION: TMOF peptide

<400> SEQUENCE: 13

Tyr Asp Pro Ala Pro Pro Pro
1               5


<210> SEQ ID NO 14
<211> LENGTH: 8
<212> TYPE: PRT
<213> ORGANISM: Artificial Sequence
<220> FEATURE:
<223> OTHER INFORMATION: TMOF peptide

<400> SEQUENCE: 14
```

-continued

Tyr Asp Pro Ala Pro Pro Pro Pro
1 5

<210> SEQ ID NO 15
<211> LENGTH: 6
<212> TYPE: PRT
<213> ORGANISM: Artificial Sequence
<220> FEATURE:
<223> OTHER INFORMATION: TMOF peptide

<400> SEQUENCE: 15

Asn Pro Thr Asn Leu His
1 5

<210> SEQ ID NO 16
<211> LENGTH: 3
<212> TYPE: PRT
<213> ORGANISM: Artificial Sequence
<220> FEATURE:
<223> OTHER INFORMATION: TMOF peptide

<400> SEQUENCE: 16

Ala Ala Pro
1

<210> SEQ ID NO 17
<211> LENGTH: 3
<212> TYPE: PRT
<213> ORGANISM: Artificial Sequence
<220> FEATURE:
<223> OTHER INFORMATION: TMOF peptide

<400> SEQUENCE: 17

Ala Asp Pro
1

<210> SEQ ID NO 18
<211> LENGTH: 5
<212> TYPE: PRT
<213> ORGANISM: Artificial Sequence
<220> FEATURE:
<223> OTHER INFORMATION: TMOF peptide

<400> SEQUENCE: 18

Ala Asp Pro Ala Pro
1 5

<210> SEQ ID NO 19
<211> LENGTH: 3
<212> TYPE: PRT
<213> ORGANISM: Artificial Sequence
<220> FEATURE:
<223> OTHER INFORMATION: TMOF peptide

<400> SEQUENCE: 19

Ala Pro Ala
1

<210> SEQ ID NO 20
<211> LENGTH: 3
<212> TYPE: PRT
<213> ORGANISM: Artificial Sequence
<220> FEATURE:
<223> OTHER INFORMATION: TMOF peptide

<400> SEQUENCE: 20

Asp Ala Ala

-continued

1

<210> SEQ ID NO 21
<211> LENGTH: 2
<212> TYPE: PRT
<213> ORGANISM: Artificial Sequence
<220> FEATURE:
<223> OTHER INFORMATION: TMOF peptide

<400> SEQUENCE: 21

Asp Phe
1

<210> SEQ ID NO 22
<211> LENGTH: 3
<212> TYPE: PRT
<213> ORGANISM: Artificial Sequence
<220> FEATURE:
<223> OTHER INFORMATION: TMOF peptide

<400> SEQUENCE: 22

Asp Pro Ala
1

<210> SEQ ID NO 23
<211> LENGTH: 2
<212> TYPE: PRT
<213> ORGANISM: Artificial Sequence
<220> FEATURE:
<223> OTHER INFORMATION: TMOF peptide

<400> SEQUENCE: 23

Asp Tyr
1

<210> SEQ ID NO 24
<211> LENGTH: 3
<212> TYPE: PRT
<213> ORGANISM: Artificial Sequence
<220> FEATURE:
<223> OTHER INFORMATION: TMOF peptide

<400> SEQUENCE: 24

Asp Tyr Pro
1

<210> SEQ ID NO 25
<211> LENGTH: 3
<212> TYPE: PRT
<213> ORGANISM: Artificial Sequence
<220> FEATURE:
<223> OTHER INFORMATION: TMOF peptide

<400> SEQUENCE: 25

Phe Ala Pro
1

<210> SEQ ID NO 26
<211> LENGTH: 3
<212> TYPE: PRT
<213> ORGANISM: Artificial Sequence
<220> FEATURE:
<223> OTHER INFORMATION: TMOF peptide

<400> SEQUENCE: 26

Phe Asp Pro
1

-continued

<210> SEQ ID NO 27
<211> LENGTH: 5
<212> TYPE: PRT
<213> ORGANISM: Artificial Sequence
<220> FEATURE:
<223> OTHER INFORMATION: TMOF peptide

<400> SEQUENCE: 27

Phe Asp Pro Ala Pro
1 5

<210> SEQ ID NO 28
<211> LENGTH: 3
<212> TYPE: PRT
<213> ORGANISM: Artificial Sequence
<220> FEATURE:
<223> OTHER INFORMATION: TMOF peptide

<400> SEQUENCE: 28

Phe Ser Pro
1

<210> SEQ ID NO 29
<211> LENGTH: 9
<212> TYPE: PRT
<213> ORGANISM: Artificial Sequence
<220> FEATURE:
<223> OTHER INFORMATION: TMOF peptide

<400> SEQUENCE: 29

Met Pro Asp Tyr Pro Pro Pro Pro Pro
1 5

<210> SEQ ID NO 30
<211> LENGTH: 3
<212> TYPE: PRT
<213> ORGANISM: Artificial Sequence
<220> FEATURE:
<223> OTHER INFORMATION: TMOF peptide

<400> SEQUENCE: 30

Pro Ala Ala
1

<210> SEQ ID NO 31
<211> LENGTH: 3
<212> TYPE: PRT
<213> ORGANISM: Artificial Sequence
<220> FEATURE:
<223> OTHER INFORMATION: TMOF peptide

<400> SEQUENCE: 31

Pro Ala Pro
1

<210> SEQ ID NO 32
<211> LENGTH: 3
<212> TYPE: PRT
<213> ORGANISM: Artificial Sequence
<220> FEATURE:
<223> OTHER INFORMATION: TMOF peptide
<220> FEATURE:
<221> NAME/KEY: MISC_FEATURE
<222> LOCATION: (2)..(2)
<223> OTHER INFORMATION: Dextrorotary Asp

<400> SEQUENCE: 32

-continued

Tyr Xaa Pro
1

<210> SEQ ID NO 33
<211> LENGTH: 5
<212> TYPE: PRT
<213> ORGANISM: Artificial Sequence
<220> FEATURE:
<223> OTHER INFORMATION: TMOF peptide
<220> FEATURE:
<221> NAME/KEY: MISC_FEATURE
<222> LOCATION: (2)..(2)
<223> OTHER INFORMATION: Dextrorotary Asp

<400> SEQUENCE: 33

Tyr Xaa Pro Ala Pro
1 5

<210> SEQ ID NO 34
<211> LENGTH: 3
<212> TYPE: PRT
<213> ORGANISM: Artificial Sequence
<220> FEATURE:
<223> OTHER INFORMATION: TMOF peptide

<400> SEQUENCE: 34

Tyr Ala Pro
1

<210> SEQ ID NO 35
<211> LENGTH: 2
<212> TYPE: PRT
<213> ORGANISM: Artificial Sequence
<220> FEATURE:
<223> OTHER INFORMATION: TMOF peptide

<400> SEQUENCE: 35

Tyr Asp
1

<210> SEQ ID NO 36
<211> LENGTH: 3
<212> TYPE: PRT
<213> ORGANISM: Artificial Sequence
<220> FEATURE:
<223> OTHER INFORMATION: TMOF peptide

<400> SEQUENCE: 36

Tyr Asp Ala
1

<210> SEQ ID NO 37
<211> LENGTH: 5
<212> TYPE: PRT
<213> ORGANISM: Artificial Sequence
<220> FEATURE:
<223> OTHER INFORMATION: TMOF peptide

<400> SEQUENCE: 37

Tyr Asp Ala Ala Pro
1 5

<210> SEQ ID NO 38
<211> LENGTH: 3
<212> TYPE: PRT
<213> ORGANISM: Artificial Sequence
<220> FEATURE:

-continued

```
<223> OTHER INFORMATION: TMOF peptide

<400> SEQUENCE: 38

Tyr Asp Phe
1


<210> SEQ ID NO 39
<211> LENGTH: 5
<212> TYPE: PRT
<213> ORGANISM: Artificial Sequence
<220> FEATURE:
<223> OTHER INFORMATION: TMOF peptide

<400> SEQUENCE: 39

Tyr Asp Phe Ala Pro
1               5


<210> SEQ ID NO 40
<211> LENGTH: 3
<212> TYPE: PRT
<213> ORGANISM: Artificial Sequence
<220> FEATURE:
<223> OTHER INFORMATION: TMOF peptide

<400> SEQUENCE: 40

Tyr Asp Gly
1


<210> SEQ ID NO 41
<211> LENGTH: 5
<212> TYPE: PRT
<213> ORGANISM: Artificial Sequence
<220> FEATURE:
<223> OTHER INFORMATION: TMOF peptide

<400> SEQUENCE: 41

Tyr Asp Leu Ala Pro
1               5


<210> SEQ ID NO 42
<211> LENGTH: 3
<212> TYPE: PRT
<213> ORGANISM: Artificial Sequence
<220> FEATURE:
<223> OTHER INFORMATION: TMOF peptide

<400> SEQUENCE: 42

Tyr Asp Pro
1


<210> SEQ ID NO 43
<211> LENGTH: 3
<212> TYPE: PRT
<213> ORGANISM: Artificial Sequence
<220> FEATURE:
<223> OTHER INFORMATION: TMOF peptide
<220> FEATURE:
<221> NAME/KEY: MISC_FEATURE
<222> LOCATION: (1)..(1)
<223> OTHER INFORMATION: Dextrorotary Tyr

<400> SEQUENCE: 43

Xaa Asp Pro
1


<210> SEQ ID NO 44
<211> LENGTH: 5
```

-continued

<212> TYPE: PRT
<213> ORGANISM: Artificial Sequence
<220> FEATURE:
<223> OTHER INFORMATION: TMOF peptide

<400> SEQUENCE: 44

Tyr Asp Pro Ala Phe
1 5

<210> SEQ ID NO 45
<211> LENGTH: 5
<212> TYPE: PRT
<213> ORGANISM: Artificial Sequence
<220> FEATURE:
<223> OTHER INFORMATION: TMOF peptide

<400> SEQUENCE: 45

Tyr Asp Pro Ala Leu
1 5

<210> SEQ ID NO 46
<211> LENGTH: 5
<212> TYPE: PRT
<213> ORGANISM: Artificial Sequence
<220> FEATURE:
<223> OTHER INFORMATION: TMOF peptide
<220> FEATURE:
<221> NAME/KEY: MISC_FEATURE
<222> LOCATION: (1)..(1)
<223> OTHER INFORMATION: Dextrorotary Tyr

<400> SEQUENCE: 46

Xaa Asp Pro Ala Pro
1 5

<210> SEQ ID NO 47
<211> LENGTH: 5
<212> TYPE: PRT
<213> ORGANISM: Artificial Sequence
<220> FEATURE:
<223> OTHER INFORMATION: TMOF peptide

<400> SEQUENCE: 47

Tyr Asp Pro Phe Pro
1 5

<210> SEQ ID NO 48
<211> LENGTH: 5
<212> TYPE: PRT
<213> ORGANISM: Artificial Sequence
<220> FEATURE:
<223> OTHER INFORMATION: TMOF peptide

<400> SEQUENCE: 48

Tyr Asp Pro Gly Pro
1 5

<210> SEQ ID NO 49
<211> LENGTH: 5
<212> TYPE: PRT
<213> ORGANISM: Artificial Sequence
<220> FEATURE:
<223> OTHER INFORMATION: TMOF peptide

<400> SEQUENCE: 49

Tyr Asp Pro Leu Pro
1 5

-continued

<210> SEQ ID NO 50
<211> LENGTH: 5
<212> TYPE: PRT
<213> ORGANISM: Artificial Sequence
<220> FEATURE:
<223> OTHER INFORMATION: TMOF peptide

<400> SEQUENCE: 50

Tyr Glu Pro Ala Pro
1 5

<210> SEQ ID NO 51
<211> LENGTH: 5
<212> TYPE: PRT
<213> ORGANISM: Artificial Sequence
<220> FEATURE:
<223> OTHER INFORMATION: TMOF peptide

<400> SEQUENCE: 51

Tyr Phe Pro Ala Pro
1 5

<210> SEQ ID NO 52
<211> LENGTH: 5
<212> TYPE: PRT
<213> ORGANISM: Artificial Sequence
<220> FEATURE:
<223> OTHER INFORMATION: TMOF peptide

<400> SEQUENCE: 52

Tyr Asn Pro Ala Pro
1 5

<210> SEQ ID NO 53
<211> LENGTH: 3
<212> TYPE: PRT
<213> ORGANISM: Artificial Sequence
<220> FEATURE:
<223> OTHER INFORMATION: TMOF peptide

<400> SEQUENCE: 53

Tyr Ser Phe
1

<210> SEQ ID NO 54
<211> LENGTH: 5
<212> TYPE: PRT
<213> ORGANISM: Artificial Sequence
<220> FEATURE:
<223> OTHER INFORMATION: TMOF peptide

<400> SEQUENCE: 54

Tyr Ser Pro Ala Pro
1 5

<210> SEQ ID NO 55
<211> LENGTH: 5
<212> TYPE: PRT
<213> ORGANISM: Artificial Sequence
<220> FEATURE:
<223> OTHER INFORMATION: TMOF peptide

<400> SEQUENCE: 55

Tyr Asp Pro Ala Ala
1 5

-continued

<210> SEQ ID NO 56
<211> LENGTH: 5
<212> TYPE: PRT
<213> ORGANISM: Artificial Sequence
<220> FEATURE:
<223> OTHER INFORMATION: TMOF peptide

<400> SEQUENCE: 56

Ala Asp Ala Ala Pro
1 5

<210> SEQ ID NO 57
<211> LENGTH: 6
<212> TYPE: PRT
<213> ORGANISM: Artificial Sequence
<220> FEATURE:
<223> OTHER INFORMATION: TMOF-R analogue peptide

<400> SEQUENCE: 57

Tyr Asp Pro Ala Pro Arg
1 5

<210> SEQ ID NO 58
<211> LENGTH: 6
<212> TYPE: PRT
<213> ORGANISM: Artificial Sequence
<220> FEATURE:
<223> OTHER INFORMATION: TMOF-R analogue peptide

<400> SEQUENCE: 58

Tyr Asp Pro Ala Phe Arg
1 5

<210> SEQ ID NO 59
<211> LENGTH: 5
<212> TYPE: PRT
<213> ORGANISM: Artificial Sequence
<220> FEATURE:
<223> OTHER INFORMATION: TMOF-R analogue peptide

<400> SEQUENCE: 59

Tyr Asp Pro Ala Arg
1 5

<210> SEQ ID NO 60
<211> LENGTH: 4
<212> TYPE: PRT
<213> ORGANISM: Artificial Sequence
<220> FEATURE:
<223> OTHER INFORMATION: TMOF-R analogue peptide

<400> SEQUENCE: 60

Asp Pro Ala Arg
1

<210> SEQ ID NO 61
<211> LENGTH: 16
<212> TYPE: PRT
<213> ORGANISM: Artificial Sequence
<220> FEATURE:
<223> OTHER INFORMATION: TMOF-R analogue peptide

<400> SEQUENCE: 61

Asp Pro Ala Arg Asp Pro Ala Arg Asp Pro Ala Arg Asp Pro Ala Arg
1 5 10 15

<210> SEQ ID NO 62

-continued

```
<211> LENGTH: 5
<212> TYPE: PRT
<213> ORGANISM: Artificial Sequence
<220> FEATURE:
<223> OTHER INFORMATION: TMOF peptide

<400> SEQUENCE: 62

Tyr Ala Pro Ala Pro
1               5


<210> SEQ ID NO 63
<211> LENGTH: 2
<212> TYPE: PRT
<213> ORGANISM: Artificial Sequence
<220> FEATURE:
<223> OTHER INFORMATION: TMOF peptide
<220> FEATURE:
<221> NAME/KEY: MISC_FEATURE
<222> LOCATION: (1)..(1)
<223> OTHER INFORMATION: Can be Ala, Asp, Phe, Met, or Tyr.
<220> FEATURE:
<221> NAME/KEY: MISC_FEATURE
<222> LOCATION: (2)..(2)
<223> OTHER INFORMATION: Can be Ala, Asp, Glu, Pro, or Tyr

<400> SEQUENCE: 63

Xaa Xaa
1
```